US012257233B2

(12) United States Patent
McKinney

(10) Patent No.: US 12,257,233 B2
(45) Date of Patent: *Mar. 25, 2025

(54) METHODS

(71) Applicant: Ethismos Research, Inc., Cambridge, MA (US)

(72) Inventor: Anthony Alexander McKinney, Boston, MA (US)

(73) Assignee: Ethismos Research, Inc., Cambridge, MA (US)

( * ) Notice: Subject to any disclaimer, the term of this patent is extended or adjusted under 35 U.S.C. 154(b) by 296 days.

This patent is subject to a terminal disclaimer.

(21) Appl. No.: 17/939,508

(22) Filed: Sep. 7, 2022

(65) Prior Publication Data

US 2023/0090174 A1    Mar. 23, 2023

Related U.S. Application Data

(63) Continuation of application No. 16/751,186, filed on Jan. 23, 2020, now Pat. No. 11,471,438, which is a continuation-in-part of application No. PCT/US2019/069143, filed on Dec. 31, 2019.

(60) Provisional application No. 62/928,294, filed on Oct. 30, 2019, provisional application No. 62/927,634, filed on Oct. 29, 2019, provisional application No. 62/787,118, filed on Dec. 31, 2018.

(51) Int. Cl.
*A61K 31/403* (2006.01)
*A61P 23/00* (2006.01)
*A61P 25/36* (2006.01)

(52) U.S. Cl.
CPC ............ *A61K 31/403* (2013.01); *A61P 23/00* (2018.01); *A61P 25/36* (2018.01)

(58) Field of Classification Search
CPC ......... A61K 31/403; A61P 25/36; A61P 23/00
See application file for complete search history.

(56) References Cited

U.S. PATENT DOCUMENTS

| | | | |
|---|---|---|---|
| 6,204,284 B1 * | 3/2001 | Beer | A61K 31/40 514/412 |
| 6,372,919 B1 | 4/2002 | Lippa et al. | |
| 7,098,229 B2 | 8/2006 | Lippa et al. | |
| 8,765,801 B2 | 7/2014 | Hagen et al. | |
| 9,139,521 B2 | 9/2015 | Hagen et al. | |
| 9,257,813 B2 | 2/2016 | Wu et al. | |
| 9,566,264 B2 | 2/2017 | Bymaster et al. | |
| 9,770,436 B2 | 9/2017 | Hagen et al. | |
| 11,471,438 B2 | 10/2022 | McKinney | |
| 2006/0020014 A1 | 1/2006 | Abou-Gharbia et al. | |
| 2006/0223875 A1 | 10/2006 | Skolnick et al. | |
| 2007/0082939 A1 | 4/2007 | Lippa et al. | |
| 2016/0346249 A1 | 12/2016 | McKinney et al. | |
| 2020/0368201 A1 | 11/2020 | McKinney | |
| 2021/0047268 A1 | 2/2021 | McKinney et al. | |
| 2021/0161863 A1 | 6/2021 | McKinney et al. | |

OTHER PUBLICATIONS

Andersen et al., "Predictive factors for the development of persistent pain after breast cancer surgery," Pain, Dec. 2015;156(12):2413-2422, DOI: 10.1097/j.pain.0000000000000298.
Bymaster et al., "Atomoxetine Increases Extracellular Levels of Norepinephrine and Dopamine in Prefrontal Cortex of Rat: A Potential Mechanism for Efficacy in Attention Deficit/Hyperactivity Disorder," Neuropsychopharmacology 2002, 27:699-711, DOI: 10.1016/S0893-133X(02)00346-9.
Cusin et al., "Ratings Scales for Depression," Handbook of Clinical Rating Scales and Assessment in Psychiatry and Mental Health, Ch. 2; L. Baer, M.A. Blais (eds.), DOI:10.1007/978-1-59745-387-5_2, 29 pgs. (2009).
Daws et al., "Unfaithful neurotransmitter transporters: Focus on serotonin uptake and implications for antidepressant efficacy," Pharmacol Ther, 2009, 121(1): 89-99, DOI: 10.1016/j.pharmthera.2008.10.004.
Erichsen et al., "Comparative actions of the opioid analgesics morphine, methadone and codeine in rat models of peripheral and central neuropathic pain," Pain, 2005, 116, pp. 347-358.
Fava et al., "Diagnosis and definition of treatment-resistant depression," Biol. Psychiatry 2003, 53, 649-659, DOI:10.1016/S0006-3223(03)00231-2.
Freeman et al., "The Triple Reuptake Inhibitor Antidepressant Effects (TRIADE) Trial: Amitifadine for the Treatment of Major Depressive Disorder," MGH Psychiatry Clinical Trials Network and Institute, Massachusetts General Hospital, Boston, Massachusetts, 1 pg. (2013).
Freeman, M. et al., "The Triple Reuptake Inhibitor Antidepressant Effects (TRIADE) Trial: Amitifadine for the Treatment of Major Depressive Disorder," American College of Neuropsychopharmacology 52nd Annual Conference, 2 pgs. (2013).
Hirschfeld, R., "Long-term side effects of SSRIs: sexual dysfunction and weight gain," J. Clin. Psychiatry 2003, 64 (Suppl. 18), pp. 20-24.
Katz et al., "Risk factors for acute pain and its persistence following breast cancer surgery," Pain, Dec. 15, 2005;119(1-3):16-25, DOI:10.1016/j.pain.2005.09.008.
Khan et al., "Catastrophizing: a predictive factor for post-operative pain," Am J Surg., Jan. 2011;201(1):122-31, DOI:10.1016/j.amjsurg.2010.02.007.
Khan et al., "Relative sensitivity of the Montgomery-Asberg Depression Rating Scale, the Hamilton Depression rating scale and the Clinical Global Impressions rating scale in antidepressant clinical trials," International Clinical Psychopharmacology 2002, 17 (6), 281-285, DOI:10.1097/00004850-200211000-00003 (Abstract).
Lesch, "Gene-environment interaction and the genetics of depression," J. Psychiatry Neurosci., 2004, 3:174-184.
Levina et al., "The Influence of Excipients on Drug Release from Hydroxypropyl Methylcellulose Matrices," Journal of Pharmaceutical Sciences 2004, 93 (11), 2746-2754, DOI:10.1002/jps.20181.
Marks et al., "Triple Reuptake Inhibitors: The Next Generation of Antidepressants," 2009, Current Neuropharmacology, 6(4), 338-43, DOI:10.2174/157015908787386078.

(Continued)

*Primary Examiner* — Timothy R Rozof
(74) *Attorney, Agent, or Firm* — ArentFox Schiff LLP; Shawn P. Foley; Chris Lorenc

(57) ABSTRACT

Provided are methods of using (1R,5S)-1-(3,4-dichlorophenyl)-3-azabicyclo[3.1.0]hexane, in free or pharmaceutically acceptable salt form.

27 Claims, 1 Drawing Sheet

(56) References Cited

OTHER PUBLICATIONS

McMillen et al., "Effect of DOV 102,677 on the Volitional Consumption of Ethanol by Myers' High Ethanol-Preferring Rat," Alcoholism Clin and Exp Res 2007, 31 (11), 1866-1871, DOI:10.1111/j.1530-0277.2007.00513.x.

NCT00659347, last updated Dec. 5, 2008, Clinical Trials.gov, https://clinicaltrials.gov/ct2/show/NCT00659347; date accessed: Nov. 15, 2022.

NCT01318434, last updated Dec. 4, 2015, Clinical Trial.gov, https://clinicaltrials.gov/ct2/show/NCT01318434; date accessed: Nov. 15, 2022.

Seminowicz et al., "Cortical responses to pain in healthy individuals depends on pain catastrophizing," Pain, Feb. 2006;120(3):297-306, DOI: 10.1016/j.pain.2005.11.008.

Sharma et al., "Triple reuptake inhibitors as potential next-generation antidepressants: a new hope?" Future Med. Chem., vol. 7, No. 17, pp. 2385-2405 (2015).

Skolnick et al., "Antidepressant-like actions of DOV 21,947: a 'triple' uptake inhibitor," European J. Pharmacology, vol. 461, pp. 99-104 (2003).

Souery et al., "Switching antidepressant class does not improve response or remission in treatment-resistant depression," J Clin Psychopharmacology, Aug. 2011;31(4):512-6, DOI:10.1097/JCP.0b013e3182228619.

Spearing et al., "Modification of the Clinical Global Impressions (CGI) scale for use in bipolar illness (BP): the CGI-BP," Psychiatry Research 1997, 73, 159-171, DOI: 10.1016/s0165-1781(97)00123-6.

Taylor et al., "Strategies for managing antidepressant-induced sexual dysfunction: systematic review of randomised controlled trials," Journal of Affective Disorders, Accepted Manuscript, vol. 88, No. 3, Elsevier, 2005, pp. 241-254, DOI:10.1016/j.jad.2005.07.006.

Tran, P. et al., "Efficacy and tolerability of the novel triple reuptake inhibitor amitifadine in the treatment of patients with major depressive disorder: A randomized, double-blind, placebo-controlled trial," Journal of Psychiatric Research, vol. 46, pp. 64-71 (2012).

Vizi et al., "Uptake and Release of Norepinephrine by Serotonergic Terminals in Norepinephrine Transporter Knock-Out Mice: Implications for the Action of Selective Serotonin Reuptake Inhibitors," J. Neurosci, 2004, 24:7888-94, DOI:10.1523/JNEUROSCI.1506-04.2004.

Wright et al., "Duloxetine in the treatment of chronic pain due to fibromyalgia and diabetic neuropathy," J. Pain Res. 2011, 4:1-10, DOI:10.2147/JPR.S12866.

Yoshii et al., "Cryptochrome Mediates Light-Dependent Magnetosensitivity of *Drosophila's* Circadian Clock," PLOS Biol., 4(7): e1000086, pp. 813-819, DOI:10.1371/journal.pbio.1000086 (Apr. 7, 2009).

Zarate et al., "A randomized trial of an N-methyl-D-aspartate antagonist in treatment-resistant major depression," Arch. Gen Psychiatry 2006, 63, 856-864, DOI: 10.1001/archpsyc.63.8.856.

Zhou et al., "Corelease of Dopamine and Serotonin from Striatal Dopamine Terminals," Neuron, 2005, 46:65-74, DOI:10.1016/j.neuron.2005.02.010.

\* cited by examiner

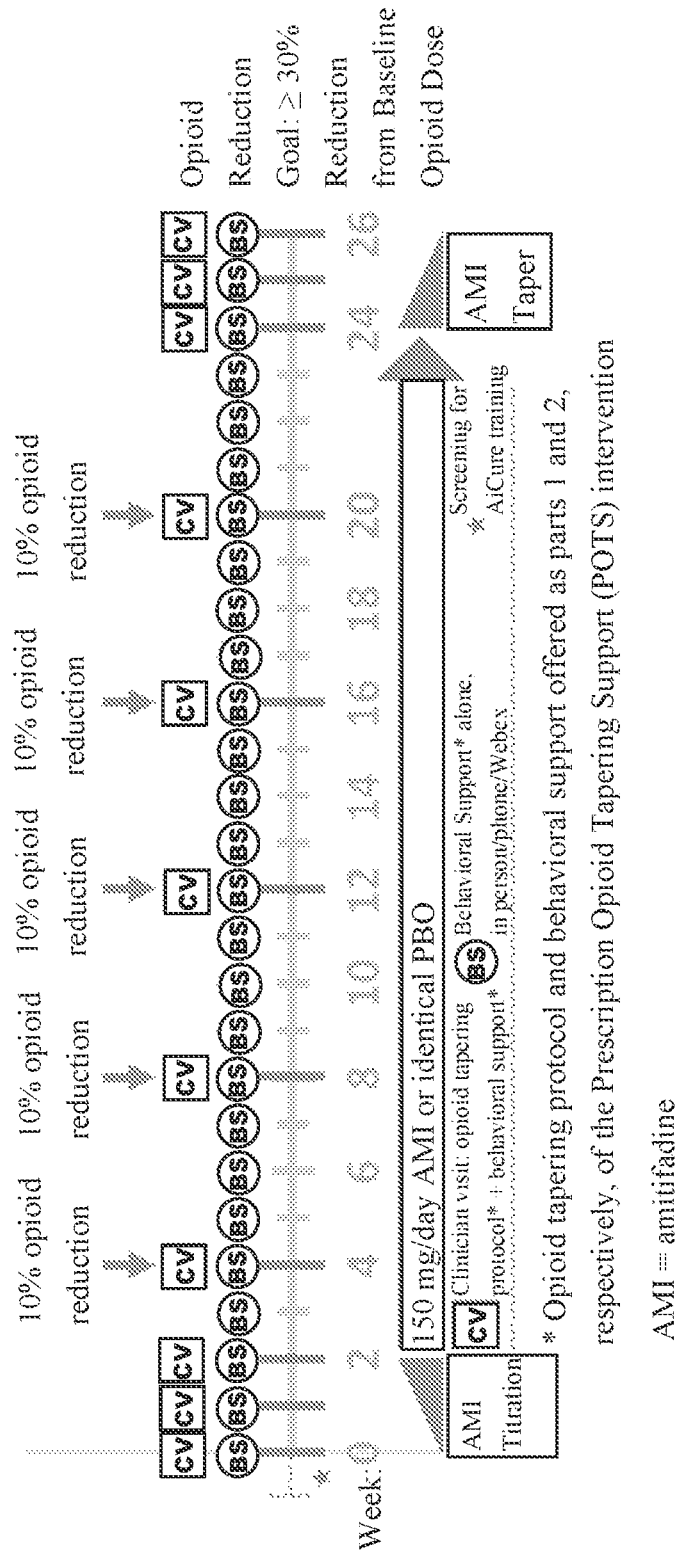

METHODS

This application is a continuation application of U.S. application Ser. No. 16/751,186, filed Jan. 23, 2020, which is a continuation-in-part of International Application No. PCT/US2019/069143 filed Dec. 31, 2019, which claims priority to U.S. Provisional Application No. 62/787,118 filed Dec. 31, 2018, U.S. Provisional Application No. 62/927,634 filed Oct. 29, 2019, and U.S. Provisional Application No. 62/928,294 filed Oct. 30, 2019, each of which are hereby incorporated by reference in their entirety.

BACKGROUND

The U.S. Centers for Disease Control and Prevention estimate there were over 70,000 opioid overdose deaths in the U.S. in 2017, an increase of about 10% over 2016. Intervention is needed to change this trend. One goal is to significantly impact the growing problem of iatrogenic opioid use disorder. Opioids are safe and effective analgesics, especially when used according to Federal Guidelines for the shortest possible durations. However, their use for chronic pain is associated with non-medical use, escalation of dose, and lethal overdose. There is evidence that use of oral opioids for pain for >90 days is associated with opioid-induced depression, opioid-induced hyperalgesia, non-medical use, opioid use disorder (OUD) or addiction, overdose and excess mortality. Patients with comorbid pain and depression may remain on opioids in an attempt to self-medicate mood and to avoid depression during opioid withdrawal. Patients with depression are more likely to drop out of opioid taper, and withdrawal symptoms during opioid taper with opioid dose reduction or discontinuation are exacerbated in patients with current depression. Opioid abuse, addiction, and overdose resulting from chronic opioid treatment are substantial public health problems. Older chronic pain patients receiving chronic opioids at high doses are at particularly high risk of death due to opioids because of overweight/obesity, sleep apnea, and reduced organ function. Negative gastrointestinal effects of opioids are well known and are exacerbated by duration and dose. While opioid antagonists with targeted gastrointestinal effects are now available, it would be preferred to minimize dose and duration of the chronic opioid agonist. Few medications are available or effective for chronic pain hence there is a critical need for non-opioid adjunctive medications with opioid-sparing effects that minimize negative opioid sequelae by enabling chronic opioid tapering.

BRIEF SUMMARY

Provided is a method of treatment for pain (e.g., chronic pain, e.g., chronic non-cancer pain) in a patient in need thereof, wherein the method comprises administering to the patient an opioid and (1R,5S)-1-(3,4-dichlorophenyl)-3-azabicyclo[3.1.0]hexane, in free or pharmaceutically acceptable salt form, wherein (1R,5S)-1-(3,4-dichlorophenyl)-3-azabicyclo[3.1.0]hexane, in free or pharmaceutically acceptable salt form, is administered in a dose sufficient to provide an opioid sparing effect (i.e., reducing the effective dose of the opioid compared to the effective dose of the opioid in a patient being treated for chronic non-cancer pain not receiving (1R,5S)-1-(3,4-dichlorophenyl)-3-azabicyclo[3.1.0]hexane, in free or pharmaceutically acceptable salt form, e.g., reducing the effective dose by at least 10%, e.g., at least 15%, 20%, 25%, 30%, 40%, or 50% or higher compared to the effective dose of the opioid in a patient being treated for chronic non-cancer pain not receiving (1R,5S)-1-(3,4-dichlorophenyl)-3-azabicyclo[3.1.0]hexane, in free or pharmaceutically acceptable salt form). For instance, the patient receiving an opioid and (1R,5S)-1-(3,4-dichlorophenyl)-3-azabicyclo[3.1.0]hexane, in free or pharmaceutically acceptable salt form, will receive less opioid (potentially including no opioid) over a period of at least 90 days of treatment, e.g., 6 months of treatment, e.g., 1 year of treatment, than a patient being treated for chronic non-cancer pain not receiving (1R,5S)-1-(3,4-dichlorophenyl)-3-azabicyclo[3.1.0]hexane, in free or pharmaceutically acceptable salt form.

Further provided is a method of reducing peak daily dose and duration of treatment with an opioid in a patient being treated with the opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of preventing an increase in daily opioid dose in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of reducing daily opioid dose increase when dose escalation is required in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of reducing daily opioid dose (e.g., tapering opioid dose, e.g., tapering and then discontinuing opioid dose) in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, provided is a method of reducing daily opioid dose (e.g., reducing daily opioid dose to 20-50 morphine milligram equivalents (MME) or less per day or reducing total daily morphine equivalent dose (MED) by at least 10%, e.g., by at least 15%, 20%, 25%, 30%, 40%, or 50%) in a patient being treated with an opioid (e.g., a patient being treated with the opioid for chronic pain, e.g., chronic non-cancer pain) for at least 90 days, wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, also provided is a method of reducing daily opioid dose and then discontinuing the opioid in a patient being treated with an opioid (e.g., a patient being treated with the opioid for chronic pain, e.g., chronic non-cancer pain, e.g., for at least 90 days), wherein the method comprises coordinately administering to the patient (1R,5S)-1-(3,4-dichlorophenyl)-3-azabicyclo[3.1.0]hexane, in free or pharmaceutically acceptable salt form, and the opioid until the opioid is discontinued and then continuing pain treatment (e.g., chronic pain, e.g., chronic non-cancer pain) with (1R,5S)-1-(3,4-dichlorophenyl)-3-azabicyclo[3.1.0]hexane, in free or pharmaceutically acceptable salt form (e.g., indefinitely).

Further provided is a method of reducing duration of opioid treatment in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid and wherein the duration of opioid treatment is reduced compared to a patient not coordinately administered (1R,5S)-1-(3,4-dichlorophenyl)-3-azabicyclo[3.1.0]hexane, in free or pharmaceutically acceptable salt form.

Further provided is a method of preventing or treating opioid use disorder or opioid misuse in a patient being treated with an opioid for chronic pain (e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of preventing or treating opioid use disorder or opioid misuse in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form.

Further provided is a method of preventing or treating one or more of opioid-induced negative affect, opioid-induced anxiety, and opioid-induced depression in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating one or more of opioid-induced negative affect, opioid-induced anxiety, and opioid-induced depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form.

Further provided is a method of preventing or treating one or more of negative affect, anxiety, and depression in a patient being treated with an opioid for chronic pain (e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, provided is a method of preventing or treating depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0] hexane, in free or pharmaceutically acceptable salt form, optionally coordinately administered with the opioid.

Further provided is a method of preventing or treating opioid-induced hyperalgesia in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced hyperalgesia in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method of non-opioid modulation (e.g., stimulation) of the periaqueductal gray (PAG) in a patient in need thereof (e.g., a patient with chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form, optionally wherein (1R,5S)-1-(3,4-dichlorophenyl)-3-azabicyclo[3.1.0]hexane, in free or pharmaceutically acceptable salt form, is coordinately administered with an opioid. For instance, provided is a method of non-opioid modulation (e.g., stimulation) of the periaqueductal gray (PAG) to reduce the perception of pain in a patient in need thereof (e.g., a patient with chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form, optionally wherein (1R,5S)-1-(3,4-dichlorophenyl)-3-azabicyclo[3.1.0]hexane, in free or pharmaceutically acceptable salt form, is coordinately administered with an opioid.

Further provided is a method of reducing withdrawal symptoms in a patient on opioid taper during opioid dose reduction or opioid discontinuation (e.g., a patient being treated with the opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form.

Further provided is a method of reducing opioid related adverse events in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of treatment for pain (e.g., chronic pain, e.g., chronic non-cancer pain) in a patient in need thereof, wherein the method comprises administering to the patient effective amounts of (1R,5S)-1-(3,4-dichlorophenyl)-3-azabicyclo[3.1.0]hexane, in free or pharmaceutically acceptable salt form, and an opioid for at least 90 days.

Further provided is a method of reducing risk of opioid overdose (e.g., preventing opioid overdose) and/or opioid use disorder in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo [3.1.0]hexane, in free or pharmaceutically acceptable salt form.

Further provided is a method of opioid discontinuation in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid until the opioid is discontinued.

Further provided is a method of reducing long-term risk of opioid use in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of reducing the frequency of increases in daily opioid dose in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of preventing or treating opioid-induced respiratory depression in a patient in need thereof (e.g., a patient who is overweight or has sleep apnea being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced respiratory depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method of preventing or treating opioid-induced gastrointestinal effects in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced gastrointestinal effects in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method of reducing risk of non-medical use of an opioid (e.g., preventing non-medical use by the patient or diversion to another) in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method of opioid discontinuation in a patient being treated for opioid addiction (e.g., a patient who has been successfully treated with an opioid (e.g., buprenorphine) for addiction (e.g., for 6 months or more, e.g., 1 year or more, e.g., 2 years or more) and is now seeking full discontinuation of opioids), wherein the method comprises administering to the patient (1R,5S)-1-(3,4-dichlorophenyl)-3-azabicyclo[3.1.0]hexane, in free or pharmaceutically acceptable salt form.

Further provided is a method of preventing or treating opioid use disorder or opioid misuse in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form.

Further provided is a method of co-administering a non-opioid medication with analgesic, antidepressant, anti-anxiety, and anti-withdrawal effects with low risk of drug:drug interactions with an opioid to a patient in need thereof (e.g., a patient being treated with an opioid for chronic pain, e.g., chronic non-cancer pain), wherein the non-opioid medication with analgesic, antidepressant, anti-anxiety, and anti-withdrawal effects is (1R,5S)-1-(3,4-dichlorophenyl)-3-azabicyclo[3.1.0]hexane, in free or pharmaceutically acceptable salt form.

Further provided is a method of preventing or treating opioid-induced loss of sexual function in a patient in need thereof (e.g., a patient being treated with an opioid for chronic pain, e.g., chronic non-cancer pain, e.g., for at least 90 days), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced loss of sexual function in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method of reducing opioid craving in a patient in need thereof (e.g., a patient being treated with an opioid for chronic pain, e.g., chronic non-cancer pain, e.g., for at least 90 days), wherein the method comprises administering to the patient (1R,5S)-1-(3,4-dichlorophenyl)-3-azabicyclo[3.1.0]hexane, in free or pharmaceutically acceptable salt form.

BRIEF DESCRIPTION OF THE DRAWINGS

FIG. 1 is a study timeline.

DETAILED DESCRIPTION

The following description of preferred embodiments is merely exemplary in nature and is in no way intended to limit this disclosure, its application, or uses.

As used throughout, ranges are used as shorthand for describing each and every value that is within the range. Any value within the range can be selected as the terminus of the range. In the event of a conflict in a definition in the present disclosure and that of a cited reference, the present disclosure controls.

(+)-1-(3,4-dichlorophenyl)-3-azabicyclo[3.1.0]hexane, also known as (1R,5S)-1-(3,4-dichlorophenyl)-3-azabicyclo[3.1.0]hexane, also known amitifadine, is shown as Formula I below.

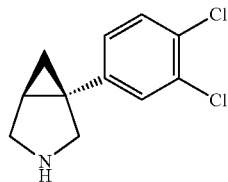

Formula I

"(+)-1-(3,4-dichlorophenyl)-3-azabicyclo[3.1.0]hexane," "(1R,5S)-1-(3,4-dichlorophenyl)-3-azabicyclo[3.1.0] hexane," and "amitifadine" are used interchangeably herein. (1R,5S)-1-(3,4-dichlorophenyl)-3-azabicyclo[3.1.0]hexane is an unbalanced triple reuptake inhibitor with the greatest potency towards serotonin reuptake (5-HT), half as much towards norepinephrine reuptake (NE), and one-eighth towards dopamine reuptake (DA). (1R,5S)-1-(3,4-dichlorophenyl)-3-azabicyclo[3.1.0]hexane hydrochloride is reported to inhibit the reuptake of [$^3$H]serotonin, [$^3$H]norepinephrine, and [$^3$H]dopamine in human embryonic kidney (HEK) 293 cells expressing the corresponding human recombinant transporters at $IC_{50}$ values of 12, 23, and 96 nm, respectively.

(1R,5S)-1-(3,4-dichlorophenyl)-3-azabicyclo[3.1.0] hexane may be synthesized as described in U.S. Pat. Nos. 6,372,919, 7,098,229, and 9,527,813, each of which are hereby incorporated by reference in their entirety.

Opioids are safe and effective analgesics, especially when used according to Federal Guidelines for the shortest possible durations. However, their use for chronic pain is associated with non-medical use, escalation of dose, and lethal overdose. For instance, it has been reported that adults with chronic pain and no substance use disorder history who are treated with opioids are at high risk for new-onset depression, with a hazard ratio for those on 90-180 days of opioid therapy of 1.25 (95% CI: 1.05-1.46) and 1.51 (95% CI: 1.31-1.74) for those on >180 days of opioids. Patients treated with opioids who develop negative affect can have increased pain sensitivity and reduced opiate responsiveness, resulting in increased opioid doses and greater risk of addiction.

Chronic opioid therapy may also induce or sensitize patients to opioid-induced hyperalgesia, which may lead to a vicious cycle of increasing dose and anxiety and, again, greater risk of addiction.

It has been estimated that 3% to 4% of U.S. adults use opioids long-term to help manage chronic pain, however, rapidly decreasing or abruptly discontinuing long-term opioid analgesics may significantly increase the risk of adverse consequences. Using the Vermont all payers database, it has been reported that >50% of patients who discontinue long-term, high-dose prescription opioids are discontinued rapidly. Among those that are discontinued, 49% subsequently have an adverse opioid-related health care event. The FDA has identified sudden opioid discontinuation as harmful and recommends gradual, individualized tapering. As described herein, amitifadine may be used to help patients (e.g., chronic non-cancer pain patients) taper their opioid dose and avoid adverse opioid-related health care events.

In patients with major depressive disorder, amitifadine has demonstrated significant antidepressant activity. In addition, (1R,5S)-1-(3,4-dichlorophenyl)-3-azabicyclo[3.1.0] hexane hydrochloride has been shown to be as effective as morphine in the second phase (15-30 minutes) of the mouse formalin paw lick test model of persistent pain.

Chronic pain is often associated with reduced dopamine transmission and amitifadine improves dopamine transmission. Patients in pain are reported to perceive greater pain because of impaired dopamine signaling and such reduced dopamine activity is reported to make pain more unpleasant. Without being bound by theory, it is believed that through improved dopamine transmission, though not such increased dopamine neurotransmission as to make amitifadine rewarding, together with improved serotonin and norepinephrine signaling, that amitifadine will cause reduced perception of pain and reduced distress due to pain. A differentiating factor between amitifadine and approved antidepressants is its potent impact on all three of serotonin, norepinephrine, and dopamine neurotransmission, thereby serving dual mood and anti-nociceptive purposes, with effects on dopamine neurotransmission ameliorating motivational and emotional aspects of pain.

By reducing breakthrough pain and depressive symptoms, patients on chronic opioid treatment for pain with adjunctive amitifadine will require fewer opioid dose escalations, experience less potential for opioid use disorder, and find opioid dose taper and discontinuation easier than patients taking an opioid not receiving adjunctive amitifadine.

Factors that make opioid tapering challenging include fear of withdrawal and acute withdrawal. Both of those may be attenuated by amitifadine, because its antidepressant properties/serotonergic properties may improve dysphoria and fear of withdrawal, and its dopaminergic properties may ameliorate any opioid withdrawal symptoms, which are in part dopamine-mediated.

In addition, amitifadine is a partial agonist at the 5-HT2c receptor. It has been proposed that serotonin exerts control of dopamine release in the ventral tegmental area via the 5-HT2c receptor. Because amitifadine is a partial agonist at the 5-HT2c receptor, it may inhibit the rewarding activity of dopamine in the ventral tegmental area, a source of euphoria with opioids. Thus, amitifadine is a desirable adjunct for use during opioid taper because it may reduce rewarding effects of opioids and thereby opioid self-administration, yet also it will not impair opioid anti-nociceptive neurotransmission. Opioid analgesic effects are manifested via the periaqueductal gray whereas reduction in self-administration results from a reduction in dopamine neurotransmission via 5-HT2c partial agonism in the ventral tegmental area.

Using amitifadine, a non-opioid adjunct capable of causing a reduction in the rewarding properties of opioids, during opioid taper makes it more likely that the opioid taper will be successful.

Methods disclosed herein prevent patients from developing opioid use disorder.

Loss of sexual function due to opioids is frequently observed. Unlike other serotonin reuptake inhibitors, amitifadine preserves sexual function.

Relevant opioids can be divided into those based on the 4,5-epoxymorphinan ring, such as morphine, buprenorphine, codeine, oxymorphone, oxycodone, hydromorphone, and hydrocodone and phenylpiperidines such as alfentanil, fentanyl, remifentanil, sufentanil, tarpentadol, and tramadol.

Most opioids undergo first-pass metabolism in the liver. Many opioids are metabolized by phase 1 metabolism (modification reactions) and other opioids are metabolized by phase 2 metabolism (conjugation). Many opioids are metabolized in phase 1 metabolism by P450 cytochrome (CYP) 2D6 and 3A4. Others, including the morphine-type, are cleared via the phase 2 route and metabolized by UGT2B7 undergo glucuronidation. Amitifadine does not interfere with those metabolic routes.

For instance, many 4,5-epoxymorphinan opioids utilize CYP2D6 and CYP3A4 metabolic routes while those with a free hydroxyl group (e.g., levorphanol, morphine, hydromorphone, and oxymorphone) may undergo glucuronidation via UGT2B7 metabolism. Phenylpiperidines use CYP3A4.

(1R,5S)-1-(3,4-dichlorophenyl)-3-azabicyclo[3.1.0] hexane may be preferred as an adjunct with chronic 4,5-epoxymorphinan-type opioids such as hydrocodone or oxycodone, which utilize CYP2D6 and CYP3A4 metabolism because amitifadine is not an inhibitor of CYP2D6 or CYP3A4. Amitifadine is also not known to be a UGT2B7 inhibitor and may be a preferred adjunct to a morphine-type opioid.

Opioid addiction, opioid abuse, opioid dependence, and opioid use disorder (e.g., mild, moderate, or severe) may be diagnosed by one of skill in the art by, for instance, referring to the Diagnostic and Statistical Manual of Mental Disorders and/or by conducting a Psychiatric Research Interview for Substance and Mental Disorders (PRISM, e.g., PRISM-5 or PRISM-Op-5) (see, e.g., Hasin, D. et al., Am J Psychiatry, 2006, 163 (4), 689-696, which is hereby incorporated by reference in its entirety). The fifth edition of the Diagnostic and Statistical Manual of Mental Disorders (DSM-5) measures opioid use disorder on a spectrum. According to the DSM-5, opioid use disorder is a problematic pattern of opioid use leading to clinically significant impairment or distress. According to the DSM-5, a diagnosis of opioid use disorder may be made if at least two of the following diagnostic criteria occur within a 12-month period:

1. Taking larger amounts or taking opioids over a longer period than intended.
2. Persistent desire or unsuccessful efforts to cut down or control opioid use.
3. Spending a great deal of time obtaining or using the opioid or recovering from its effects.
4. Craving, or a strong desire or urge to use opioids.
5. Problems fulfilling obligations at work, school or home.
6. Continued opioid use despite having recurring social or interpersonal problems.
7. Giving up or reducing activities because of opioid use.
8. Using opioids in physically hazardous situations.
9. Continued opioid use despite ongoing physical or psychological problem likely to have been caused or worsened by opioids.
10. Tolerance, which is 1) a need for increased amounts of opioids and/or 2) diminished effect with continued use of the same amount.
11. Experiencing withdrawal (opioid withdrawal syndrome, see below) and/or taking opioids (or a closely related substance) to relieve or avoid withdrawal symptoms.
    Opioid withdrawal syndrome:
    A) Either of the following: 1) Cessation of (or reduction in) opioid use that has been heavy and prolonged (several weeks or longer), or 2) administration of an opioid antagonist after a period of opioid use and
    B) Three (or more) of the following, developing within minutes to several days after Criterion A: dysphoric mood; nausea or vomiting; muscle aches; lacrimation or rhinorrhea; pupillary dilation, piloerection, or sweating; diarrhea; yawning; fever; or insomnia.

Another way of formulating the DSM-5 diagnostic criteria for opioid use disorder is if at least two of the following occur within a 12-month period:

1. Opioids are often taken in larger amounts or over a longer period than was intended.
2. There is a persistent desire or unsuccessful efforts to cut down or control opioid use.
3. A great deal of time is spent in activities necessary to obtain the opioid, use the opioid, or recover from its effects.
4. Craving, or a strong desire or urge to use opioids.
5. Recurrent opioid use resulting in a failure to fulfill major role obligations at work, school, or home.
6. Continued opioid use despite having persistent or recurrent social or interpersonal problems caused or exacerbated by the effects of opioids.
7. Important social, occupational, or recreational activities are given up or reduced because of opioid use.
8. Recurrent opioid use in situations in which it is physically hazardous.
9. Continued opioid use despite knowledge of having a persistent or recurrent physical or psychological problem that is likely to have been caused or exacerbated by the substance.
10. Exhibits tolerance, which is 1) a need for markedly increased amounts of opioids to achieve intoxication or desired effect and/or 2) a markedly diminished effect with continued use of the same amount of an opioid.
11. Exhibits withdrawal (opioid withdrawal syndrome, see below) and/or taking opioids (or a closely related substance) to relieve or avoid withdrawal symptoms.
    Opioid withdrawal syndrome:
    A) Either of the following: 1) Cessation of (or reduction in) opioid use that has been heavy and prolonged (several weeks or longer), or 2) administration of an opioid antagonist after a period of opioid use and
    B) Three (or more) of the following, developing within minutes to several days after Criterion A: dysphoric mood; nausea or vomiting; muscle aches; lacrimation or rhinorrhea; pupillary dilation, piloerection, or sweating; diarrhea; yawning; fever; or insomnia.

The last two diagnostic criteria (numbers ten and eleven in both of the above), related to tolerance and withdrawal, are not considered to be met for individuals taking opioids solely under appropriate medical supervision. A patient with mild opioid use disorder may exhibit 2-3 of the above criteria, a patient with moderate opioid use disorder may exhibit 4-5 of the above criteria, and a patient with severe opioid use disorder may exhibit 6 or more of the above criteria.

As used herein, each of "(+)-1-(3,4-dichlorophenyl)-3-azabicyclo[3.1.0]hexane," "(1R,5S)-1-(3,4-dichlorophenyl)-3-azabicyclo[3.1.0]hexane," and "amitifadine" embrace the compound in any form, for example, free or pharmaceutically acceptable salt form, e.g., as a pharmaceutically acceptable acid addition salt. Pharmaceutically acceptable salts are known in the art and include salts that are physiologically acceptable at the dosage amount and form to be administered, for example, hydrochloride salts.

As used herein, each of "(+)-1-(3,4-dichlorophenyl)-3-azabicyclo[3.1.0]hexane," "(1R,5S)-1-(3,4-dichlorophenyl)-3-azabicyclo[3.1.0]hexane," and "amitifadine" are also to be understood as embracing the compound in crystalline and amorphous form including, for example, polymorphs, solvates (including hydrates), unsolvated polymorphs (including anhydrates), conformational polymorphs, and amorphous forms of the compounds, as well as mixtures thereof. "Crystalline form" and "polymorph" may be used interchangeably herein, and are meant to include all crystalline forms of (1R,5S)-1-(3,4-dichlorophenyl)-3-azabicyclo[3.1.0]hexane, in free or pharmaceutically acceptable salt form, including, for example, polymorphs, solvates (including hydrates), unsolvated polymorphs (including anhydrates), and conformational polymorphs, as well as mixtures thereof, unless a particular crystalline form is referred to.

(1R,5S)-1-(3,4-dichlorophenyl)-3-azabicyclo[3.1.0] hexane hydrochloride exists in at least three polymorphic forms, labeled polymorphs A, B, and C, as disclosed in U.S.

Pat. Nos. 8,765,801, 9,139,521, and 9,770,436, each of which are hereby incorporated by reference in their entirety.

Crystalline and amorphous forms of (1R,5S)-1-(3,4-dichlorophenyl)-3-azabicyclo[3.1.0]hexane, in free or pharmaceutically acceptable salt form, may be used in any combination or in forms that are substantially free of one or more of the other crystalline forms or free of the amorphous form.

As used herein, "substantially free of other polymorphic forms" means that the crystalline material contains no more than 5% w/w of any other crystalline form, e.g., no more than 2% w/w of any other crystalline form, e.g., no more than 1% w/w of any other crystalline form.

As used herein, "chronic pain" includes nociceptive or neuropathic pain that lasts for greater than 90 days and/or extends beyond the expected period of healing.

(1R,5S)-1-(3,4-dichlorophenyl)-3-azabicyclo[3.1.0] hexane may in some cases also exist in prodrug form. Prodrugs are considered to be any covalently bonded carriers that release the active parent drug in vivo.

As used herein, "effective amount" refers to an amount effective, when administered to a patient, to provide a therapeutic benefit such as reducing pain. The specific dose of substance(s) (e.g., (1R,5S)-1-(3,4-dichlorophenyl)-3-azabicyclo[3.1.0]hexane, in free or pharmaceutically acceptable salt form and/or opioid) administered to obtain a therapeutic benefit will, of course, be determined by the particular circumstances surrounding the case, including, for example, the route of administration and individual being treated.

Where two active agents are administered, the effective amount of each agent may be below the amount needed for activity of each as a monotherapy. Accordingly, a subthreshold amount (i.e., an amount below the level necessary for efficacy as monotherapy) may be an effective amount.

As used herein, "coordinately administering" means the treatments are administered within the same therapeutic regimen. The individual treatments may be dosed separately or together (e.g., simultaneously or within the same composition).

As used herein, "opioid related adverse events" include hyperalgesia, nausea, vomiting, constipation, urinary retention, sedation, somnolence, headache, dizziness, pruritus, respiratory depression, dry mouth, cognitive impairment, tolerance, or dependence.

As used herein, "opioid" includes prescription opioids such as hydrocodone (Vicodin®), oxycodone (OxyContin®, Percocet®), oxymorphone (Opana®), morphine (Kadian®, Avinza®), codeine, fentanyl, and levorphanol. Tramadol, dihydrocodeine, meperidine, hydromorphone, tapentadol, remifentanil, buprenorphine, alfentanil, carfentanil, and sufentanil are also opioids. Opana® is tablets of oxymorphone hydrochloride. Vicodin® includes hydrocodone bitartrate. Percocet® contains oxycodone hydrochloride. In the human body, hydromorphone is formed from the O-demethylation of hydrocodone and may contribute to the total analgesic effect of hydrocodone, and codeine is converted to morphine. So, "opioid" embraces free and pharmaceutically acceptable salt forms (e.g., oxymorphone hydrochloride, hydrocodone bitartrate) and prodrug forms (e.g., benzhydrocodone).

Morphine milligram equivalents or morphine equivalent dose may be calculated by, for instance, the U.S. Centers for Disease Control (CDC) and Prevention Morphine Milligram Equivalent (MME) calculator or by referring to, for instance, the U.S. Centers for Disease Control and Prevention MME conversion factors (see, e.g., National Center for Injury Prevention and Control. CDC compilation of benzodiazepines, muscle relaxants, stimulants, zolpidem, and opioid analgesics with oral morphine milligram equivalent conversion factors, 2018 version. Atlanta, GA: Centers for Disease Control and Prevention, which is hereby incorporated by reference in its entirety, available on the CDC website). To convert to morphine milligram equivalents (MME), multiply the dose for an opioid by the conversion factor. According to the CDC, morphine milligram equivalent (MME) conversion factors are:

| Opioid | Oral MME Conversion Factor |
| --- | --- |
| Codeine | 0.15 |
| Fentanyl transdermal (in mcg/hr) | 2.4 (7.2 for a fentanyl patch that remains in place for 3 days) |
| Hydrocodone | 1 |
| Hydromorphone | 4 |
| Morphine | 1 |
| Oxycodone | 1.5 |
| Oxymorphone | 3 |

Conversion factors may be used in the formula:
strength per unit×(number of units/days supply)×MME conversion factor=MME/day Opioid craving may be measured on a scale of 0 (not at all) to 10 (extremely) (see, e.g., McHugh, R. et al., Drug and Alcohol Dependence, 2014, 145, 121-126, which is hereby incorporated by reference in its entirety). Relapse to prescription opioid abuse may be predicted by measuring prescription opioid craving.

Provided is a method (Method 1) of treatment for pain (e.g., chronic pain, e.g., chronic non-cancer pain) in a patient in need thereof, wherein the method comprises administering to the patient an opioid and (1R,5S)-1-(3,4-dichlorophenyl)-3-azabicyclo[3.1.0]hexane, in free or pharmaceutically acceptable salt form, wherein (1R,5S)-1-(3,4-dichlorophenyl)-3-azabicyclo[3.1.0]hexane, in free or pharmaceutically acceptable salt form, is administered in a dose sufficient to provide an opioid sparing effect (i.e., reducing the effective dose of the opioid compared to the effective dose of the opioid in a patient being treated for chronic non-cancer pain not receiving (1R,5S)-1-(3,4-dichlorophenyl)-3-azabicyclo[3.1.0]hexane, in free or pharmaceutically acceptable salt form, e.g., reducing the effective dose by at least 10%, e.g., at least 15%, 20%, 25%, 30%, 40%, or 50% or higher compared to the effective dose of the opioid in a patient being treated for chronic non-cancer pain not receiving (1R,5S)-1-(3,4-dichlorophenyl)-3-azabicyclo[3.1.0]hexane, in free or pharmaceutically acceptable salt form). For instance, the patient receiving an opioid and (1R,5S)-1-(3,4-dichlorophenyl)-3-azabicyclo[3.1.0]hexane, in free or pharmaceutically acceptable salt form, will receive less opioid (potentially including no opioid) over a period of at least 90 days of treatment, e.g., 6 months of treatment, e.g., 1 year of treatment, than a patient being treated for chronic non-cancer pain not receiving (1R,5S)-1-(3,4-dichlorophenyl)-3-azabicyclo[3.1.0]hexane, in free or pharmaceutically acceptable salt form.

Further provided is a method (Method 2) of reducing peak daily dose and duration of treatment with an opioid in a patient being treated with the opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 3) of preventing an increase in daily opioid dose in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 4) of reducing daily opioid dose increase when dose escalation is required in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 5) of reducing daily opioid dose (e.g., tapering opioid dose, e.g., tapering and then discontinuing opioid dose) in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, provided is a method of reducing daily opioid dose (e.g., reducing daily opioid dose to 20-50 morphine milligram equivalents (MME) or less per day or reducing total daily morphine equivalent dose (MED) by at least 10%, e.g., by at least 15%, 20%, 25%, 30%, 40%, or 50%) in a patient being treated with an opioid (e.g., a patient being treated with the opioid for chronic pain, e.g., chronic non-cancer pain) for at least 90 days, wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, also provided is a method of reducing daily opioid dose and then discontinuing the opioid in a patient being treated with an opioid (e.g., a patient being treated with the opioid for chronic pain, e.g., chronic non-cancer pain, e.g., for at least 90 days), wherein the method comprises coordinately administering to the patient (1R,5S)-1-(3,4-dichlorophenyl)-3-azabicyclo[3.1.0]hexane, in free or pharmaceutically acceptable salt form, and the opioid until the opioid is discontinued and then continuing pain treatment (e.g., chronic pain, e.g., chronic non-cancer pain) with (1R,5S)-1-(3,4-dichlorophenyl)-3-azabicyclo[3.1.0]hexane, in free or pharmaceutically acceptable salt form (e.g., indefinitely).

Further provided is a method (Method 6) of reducing duration of opioid treatment in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid and wherein the duration of opioid treatment is reduced compared to a patient not coordinately administered (1R,5S)-1-(3,4-dichlorophenyl)-3-azabicyclo[3.1.0]hexane, in free or pharmaceutically acceptable salt form.

Further provided is a method (Method 7) of preventing or treating opioid use disorder or opioid misuse in a patient being treated with an opioid for chronic pain (e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 8) of preventing or treating opioid use disorder or opioid misuse in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form.

Further provided is a method (Method 9) of preventing or treating one or more of opioid-induced negative affect, opioid-induced anxiety, and opioid-induced depression in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating one or more of opioid-induced negative affect, opioid-induced anxiety, and opioid-induced depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form.

Further provided is a method (Method 10) of preventing or treating one or more of negative affect, anxiety, and depression in a patient being treated with an opioid for chronic pain (e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid. For instance, provided is a method of preventing or treating depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method (Method 11) of preventing or treating opioid-induced hyperalgesia in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced hyperalgesia in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method (Method 12) of non-opioid modulation (e.g., stimulation) of the periaqueductal gray (PAG) in a patient in need thereof (e.g., a patient with chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form, optionally wherein (1R,5S)-1-(3,4-dichlorophenyl)-3-azabicyclo[3.1.0]hexane, in free or pharmaceutically acceptable salt form, is coordinately administered with an opioid. For instance, provided is a method of non-opioid modulation (e.g., stimulation) of the periaqueductal gray (PAG) to reduce the perception of pain in a patient in need thereof (e.g., a patient with chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form, optionally wherein (1R,5S)-1-(3,4-dichlorophenyl)-3-azabicyclo[3.1.0]hexane, in free or pharmaceutically acceptable salt form, is coordinately administered with an opioid.

Further provided is a method (Method 13) of reducing withdrawal symptoms in a patient on opioid taper during opioid dose reduction or opioid discontinuation (e.g., a patient being treated with the opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form.

Further provided is a method (Method 14) of reducing opioid related adverse events in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 15) of treatment for pain (e.g., chronic pain, e.g., chronic non-cancer pain) in a patient in need thereof, wherein the method comprises administering to the patient effective amounts of (1R,5S)-1-(3,4-dichlorophenyl)-3-azabicyclo[3.1.0]hexane, in free or pharmaceutically acceptable salt form, and an opioid for at least 90 days.

Further provided is a method (Method 16) of reducing risk of opioid overdose (e.g., preventing opioid overdose) and/or opioid use disorder in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form.

Further provided is a method (Method 17) of opioid discontinuation in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid until the opioid is discontinued.

Further provided is a method (Method 18) of reducing long-term risk of opioid use in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 19) of reducing the frequency of increases in daily opioid dose in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 20) of preventing or treating opioid-induced respiratory depression in a patient in need thereof (e.g., a patient who is overweight or has sleep apnea being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced respiratory depression in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method (Method 21) of preventing or treating opioid-induced gastrointestinal effects in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced gastrointestinal effects in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method (Method 22) of reducing risk of non-medical use of an opioid (e.g., preventing non-medical use by the patient or diversion to another) in a patient being treated with an opioid (e.g., a patient being treated with the opioid for chronic pain, e.g., chronic non-cancer pain), wherein the method comprises coordinately administering to the patient (1R,5S)-1-(3,4-dichlorophenyl)-3-azabicyclo[3.1.0]hexane, in free or pharmaceutically acceptable salt form, and the opioid.

Further provided is a method (Method 23) of opioid discontinuation in a patient being treated for opioid addiction (e.g., a patient who has been successfully treated with an opioid (e.g., buprenorphine) for addiction (e.g., for 6 months or more, e.g., 1 year or more, e.g., 2 years or more) and is now seeking full discontinuation of opioids), wherein the method comprises administering to the patient (1R,5S)-1-(3,4-dichlorophenyl)-3-azabicyclo[3.1.0]hexane, in free or pharmaceutically acceptable salt form.

Further provided is a method (Method 24) of preventing or treating opioid use disorder or opioid misuse (e.g., a method of preventing opioid misuse) in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing opioid use disorder or opioid misuse (e.g., a method of preventing opioid use disorder) in a patient in need thereof (e.g., a patient being treated with an opioid for chronic pain, e.g., chronic non-cancer pain), wherein the method comprises administering to the patient (1R,5S)-1-(3,4-dichlorophenyl)-3-azabicyclo[3.1.0]hexane, in free or pharmaceutically acceptable salt form.

Further provided is a method (Method 25) of co-administering a non-opioid medication with analgesic, antidepressant, anti-anxiety, and anti-withdrawal effects with low risk of drug:drug interactions with an opioid to a patient in need thereof (e.g., a patient being treated with an opioid for chronic pain, e.g., chronic non-cancer pain), wherein the non-opioid medication with analgesic, antidepressant, anti-anxiety, and anti-withdrawal effects is (1R,5S)-1-(3,4-dichlorophenyl)-3-azabicyclo[3.1.0]hexane, in free or pharmaceutically acceptable salt form.

Further provided is a method (Method 26) of preventing or treating opioid-induced loss of sexual function in a patient in need thereof (e.g., a patient being treated with an opioid for chronic pain, e.g., chronic non-cancer pain, e.g., for at least 90 days), wherein the method comprises administering to the patient (1R,5S)-1-(3,4-dichlorophenyl)-3-azabicyclo[3.1.0]hexane, in free or pharmaceutically acceptable salt form. For instance, provided is a method of preventing or treating opioid-induced loss of sexual function in a patient who has taken or is expected to take an opioid for at least 90 days (e.g., a patient being treated with the opioid for chronic pain (e.g., chronic non-cancer pain)), wherein the method comprises administering to the patient (1R,5S)-1-(3,4-dichlorophenyl)-3-azabicyclo[3.1.0]hexane, in free or pharmaceutically acceptable salt form, optionally coordinately administered with the opioid.

Further provided is a method (Method 27) of reducing opioid craving in a patient in need thereof (e.g., a patient being treated with an opioid for chronic pain, e.g., chronic non-cancer pain, e.g., for at least 90 days), wherein the method comprises administering to the patient (1R,5S)-1-(3,4-dichlorophenyl)-3-azabicyclo[3.1.0]hexane, in free or pharmaceutically acceptable salt form.

Further provided is any of Method 1-27 as follows:

1.1 Any of Method 1-27, wherein (1R,5S)-1-(3,4-dichlorophenyl)-3-azabicyclo[3.1.0]hexane is in pharmaceutically acceptable salt form.

1.2 Any Method 1-27 or 1.1, wherein (1R,5S)-1-(3,4-dichlorophenyl)-3-azabicyclo[3.1.0]hexane in pharmaceutically acceptable salt form is an acid addition salt.

1.3 Any of Method 1-27, 1.1, or 1.2, wherein (1R,5S)-1-(3,4-dichlorophenyl)-3-azabicyclo[3.1.0]hexane in pharmaceutically acceptable salt form is (1R,5S)-1-(3,4-dichlorophenyl)-3-azabicyclo[3.1.0]hexane hydrochloride.

1.4 Any of Method 1-27 or 1.1-1.3, wherein (1R,5S)-1-(3,4-dichlorophenyl)-3-azabicyclo[3.1.0]hexane in pharmaceutically acceptable salt form is crystalline.

1.5 Any of Method 1-27 or 1.1-1.4, wherein (1R,5S)-1-(3,4-dichlorophenyl)-3-azabicyclo[3.1.0]hexane, in free or pharmaceutically acceptable salt form, is Polymorph A, for example, Polymorph A substantially free of other polymorphic forms.

1.6 Any of Method 1-27 or 1.1-1.4, wherein (1R,5S)-1-(3,4-dichlorophenyl)-3-azabicyclo[3.1.0]hexane, in free or pharmaceutically acceptable salt form, is Polymorph B, for example, Polymorph B substantially free of other polymorphic forms.

1.7 Any of Method 1-27 or 1.1-1.4, wherein (1R,5S)-1-(3,4-dichlorophenyl)-3-azabicyclo[3.1.0]hexane, in free or pharmaceutically acceptable salt form, is Polymorph C, for example, Polymorph C substantially free of other polymorphic forms.

1.8 Any of Method 1-27 or 1.1-1.7, wherein the method comprises administering (1R,5S)-1-(3,4-dichlorophenyl)-3-azabicyclo[3.1.0]hexane, in free or pharmaceutically acceptable salt form, once, twice, three, or four times daily, e.g., once daily, e.g., twice daily, e.g., three times daily, e.g., four times daily.

1.9 Any of Method 1-27 or 1.1-1.8, wherein the method comprises administering 75 mg to 200 mg of (1R,5S)-1-(3,4-dichlorophenyl)-3-azabicyclo[3.1.0]hexane, in free or pharmaceutically acceptable salt form, per day, for example, comprising administering 100 mg to 200 mg of (1R,5S)-1-(3,4-dichlorophenyl)-3-azabicyclo[3.1.0]hexane, in free or pharmaceutically acceptable salt form, per day, for example, comprising administering 150 mg of (1R,5S)-1-(3,4-dichlorophenyl)-3-azabicyclo[3.1.0]hexane, in free or pharmaceutically acceptable salt form, per day (e.g., by administering 75 mg twice per day, e.g., by administering three 25 mg tablets in the morning and three 25 mg tablets in the afternoon).

1.10 Any of Method 1-27 or 1.1-1.9, wherein the pain is chronic pain, e.g., chronic non-cancer pain. For instance, any of Method 1-27 or 1.1-1.9, wherein the pain is chronic musculoskeletal pain (e.g., degenerative disease of the spine, osteoarthritis, or axial back pain). For instance, any of Method 1-27 or 1.1-1.9, wherein the pain is chronic back, chronic neck, chronic joint, or chronic limb pain, e.g., chronic back, chronic neck, or chronic joint pain.

1.11 Any of Method 1-7, 9-14, 16-27, or 1.1-1.10, wherein the patient has taken or is expected to take the opioid for at least 2 weeks, e.g., at least 6 weeks, e.g., at least 90 days, e.g., greater than 90 days, e.g., at least 12 weeks, e.g., at least 6 months, e.g., at least 1 year, e.g., greater than 1 year, e.g., at least 18 months, e.g., at least 2 years. For instance, any of Method 1-7, 9-14, 16-27, or 1.1-1.10, wherein the patient has taken or is expected to take the opioid for at least 3 months (e.g., greater than 3 months). Any of Method 8, 15, or 1.1-1.10, wherein the patient has taken or is expected to take the opioid for greater than 90 days, e.g., at least 12 weeks, e.g., at least 6 months, e.g., at least 1 year, e.g., greater than 1 year, e.g., at least 18 months, e.g., at least 2 years.

1.12 Any of Method 1-22, 24-27, or 1.1-1.11, wherein the opioid is a full opioid agonist.

1.13 Any of Method 1-22, 24-27, or 1.1-1.12, wherein the opioid is hydrocodone, oxycodone, oxymorphone, morphine, codeine, fentanyl, or levorphanol. For instance, any of Method 1-22, 24-27, or 1.1-1.12, wherein the opioid is hydrocodone, oxycodone, oxymorphone, hydromorphone, morphine, codeine, fentanyl, or remifentanil. For instance, any of Method 1-22, 24-27, or 1.1-1.12, wherein the opioid is hydrocodone. Or, for instance, any of Method 1-22, 24-27, or 1.1-1.12, wherein the opioid is oxycodone. Or any of Method 1-22, 24-27, or 1.1-1.12, wherein the opioid is a 4,5-epoxymorphinan-type opioid (e.g., hydrocodone or oxycodone) and/or a phenylpiperidine-type opioid (e.g., fentanyl). For instance, any of Method 1-22, 24-27, or 1.1-1.12, wherein the opioid is a 4,5-epoxymorphinan-type opioid (e.g., hydrocodone or oxycodone). Or, for instance, any of Method 1-22, 24-27, or 1.1-1.12, wherein the opioid is a phenylpiperidine-type opioid. Or, for instance, any of Method 1-22, 24-27, or 1.1-1.12, wherein the opioid has a low risk of drug-drug interaction (e.g., because of its metabolic pathway) with (1R,5S)-1-(3,4-dichlorophenyl)-3-azabicyclo[3.1.0]hexane, in free or pharmaceutically acceptable salt form. The opioid (e.g., hydrocodone and/or oxycodone) may be in free or pharmaceutically acceptable salt form (e.g., hydrocodone and/or oxycodone, in free or pharmaceutically acceptable salt form, e.g., oxymorphone hydrochloride, hydrocodone bitartrate), or prodrug form.

1.14 Any of Method 1 or 1.1-1.13, wherein the method comprises reducing the effective dose of the opioid by at least 10%, e.g., by at least 15%, 20%, 25%, 30%, 40%, or 50%, e.g., by at least 30%, e.g., by 30%.

1.15 Any of Method 1 or 1.1-1.14, wherein the method comprises reducing the effective dose of the opioid to 50 morphine milligram equivalents (MME) or less per day, e.g., 20-50 MME per day, e.g., 40 MME or less per day, e.g., 20-40 MME per day, e.g., 20-30 MME per day. For instance, wherein the method comprises reducing the effective dose of the opioid to 20 morphine milligram equivalents (MME) or less per day, e.g., 1-20 MME per day. Or, for instance, wherein the method comprises reducing the effective dose of the opioid to less than 20 morphine milligram equivalents (MME) per day.

1.16 Any of Method 1 or 1.1-1.15, wherein the method comprises reducing the effective dose of the opioid to 1-40 morphine milligram equivalents (MME) per day, e.g., 1-36 MME per day, e.g., 1-20 MME per day, e.g., 10-20 MME per day.

1.17 Any of Method 2 or 1.1-1.13, wherein the method comprises reducing peak daily dose of an opioid in a patient being treated with the opioid.

1.18 Any of Method 2, 1.1-1.13, or 1.17, wherein the method comprises reducing duration of exposure to an opioid in a patient being treated with the opioid.

1.19 Any of Method 2, 1.1-1.13, 1.17, or 1.18, wherein the peak daily dose of the opioid is reduced by at least 10%, e.g., by at least 15%, 20%, 25%, 30%, 40%, or 50%, e.g., by at least 30%, e.g., by 30%. For instance, wherein after 4 weeks, 8 weeks, 90 days, 6 months, 1 year, or 18 months of receiving (1R,5S)-1-(3,4-dichlorophenyl)-3-azabicyclo[3.1.0]hexane, in free or pharmaceutically acceptable salt form, the peak daily dose is reduced by at least 10%, e.g., by at least 15%, 20%, 25%, 30%, 40%, or 50%, e.g., by at least 30%, e.g., by 30%. For instance, wherein after 4 weeks of receiving (1R,5S)-1-(3,4-dichlorophenyl)-3-azabicyclo[3.1.0]hexane, in free or pharmaceutically acceptable salt form, the peak daily dose is reduced by at least 10% (e.g., by 10%), and further optionally after 8 weeks of receiving (1R,5S)-1-(3,4-dichlorophenyl)-3-azabicyclo[3.1.0]hexane, in free or pharmaceutically acceptable salt form, the peak daily dose is reduced by at least 20% (e.g., by 20%), and further optionally after 12 weeks of receiving (1R,5S)-1-(3,4-dichlorophenyl)-3-azabicyclo[3.1.0]hexane, in free or pharmaceutically acceptable salt form, the peak daily dose is reduced by at least 30% (e.g., by 30%), and further optionally after 16 weeks of receiving (1R,5S)-1-(3,4-dichlorophenyl)-3-azabicyclo[3.1.0]hexane, in free or pharmaceutically acceptable salt form, the peak daily dose is reduced by at least 40% (e.g., by 40%), and further optionally after 20 weeks of receiving (1R,5S)-1-(3,4-dichlorophenyl)-3-azabicyclo[3.1.0]hexane, in free or pharmaceutically acceptable salt form, the peak daily dose is reduced by at least 50% (e.g., by 50%). Or, for instance, wherein within or after at least 5 months (e.g., 6 months) of receiving (1R,5S)-1-(3,4-dichlorophenyl)-3-azabicyclo[3.1.0]hexane, in free or pharmaceutically acceptable salt form, the peak daily dose of the opioid is reduced by at least 10%, e.g., by at least 30% (e.g., by 30%), e.g., by at least 40% (e.g., by 40%), e.g., by at least 50% (e.g., by 50%). For instance, wherein within or after 6 months of receiving (1R,5S)-1-(3,4-dichlorophenyl)-3-azabicyclo[3.1.0]hexane, in free or pharmaceutically acceptable salt form, the peak daily dose of the opioid is reduced by at least 30% (e.g., by 30%), e.g., by at least 40% (e.g., by 40%).

1.20 Any of Method 2, 1.1-1.13, or 1.17-1.19, wherein the peak daily dose of the opioid is reduced by 2% to 10% over 4 to 8 weeks. For instance, wherein the peak daily dose is reduced by 10% over 4 weeks. For instance, wherein the peak daily dose is reduced by 10% over 8 weeks.

1.21 Any of Method 2, 1.1-1.13, or 1.17-1.19, wherein the peak daily dose of the opioid is reduced by 5% to 20% over 4 weeks.

1.22 Any of Method 2, 1.1-1.13, or 1.17-1.19, wherein the peak daily dose of the opioid is reduced by 10% to 20% in a week.

1.23 Any of Method 2, 1.1-1.13, or 1.17-1.19, wherein the peak daily dose of the opioid is reduced by 20% to 50% and then reduced by 10% to 20% daily.

1.24 Any of Method 2, 1.1-1.13, or 1.17-1.23, wherein the peak daily dose is 50 morphine milligram equivalents (MME) or more per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the peak daily dose is more than 50 to less than 90 MME per day. Or, for instance, wherein the peak daily dose is 50 morphine milligram equivalents (MME) or more per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.25 Any of Method 2-22, 24-27, 1.1-1.13, or 1.17-1.24, wherein the method comprises maintaining the opioid dose at or reducing the opioid dose to 50 morphine milligram equivalents (MME) or less per day, e.g., 20-50 MME per day, e.g., 40 MME or less per day, e.g., 20-40 MME per day, e.g., 20-30 MME per day. For instance, wherein the method comprises maintaining the opioid dose at or reducing the opioid dose to 20 morphine milligram equivalents (MME) or less per day, e.g., 1-20 MME per day. Or, for instance, wherein the method comprises maintaining the opioid dose at or reducing the opioid dose to less than 20 morphine milligram equivalents (MME) per day.

1.26 Any of Method 2-22, 24-27, 1.1-1.13, or 1.17-1.25, wherein the method comprises maintaining the opioid dose at or reducing the opioid dose to 1-40 morphine milligram equivalents (MME) per day, e.g., 1-36 MME per day, e.g., 1-20 MME per day, e.g., 10-20 MME per day.

1.27 Any of Method 2, 1.1-1.13, or 1.17-1.26, wherein the duration of treatment with the opioid is reduced to 2 years or less, e.g., 18 months or less, e.g., 1 year or less, e.g., 6 months or less.

1.28 Any of Method 2, 1.1-1.13, or 1.17-1.27, wherein the duration of treatment with the opioid is reduced to 3 months or less.

1.29 Any of Method 2, 1.1-1.13, or 1.17-1.28, wherein the duration of treatment with the opioid is reduced to 6 weeks or less.

1.30 Any of Method 2, 1.1-1.13, or 1.17-1.29, wherein the duration of treatment with the opioid is reduced to 2 weeks or less.

1.31 Any of Method 3, 1.1-1.13, 1.25, or 1.26, wherein the current opioid dose not to be increased is 50 morphine milligram equivalents (MME) or less per day, e.g., 20-50 MME per day, e.g., 40 MME or less per day, e.g., 20-40 MME per day, e.g., 20-30 MME per day. For instance, wherein the current opioid dose not to be increased is 20 morphine milligram equivalents (MME) or less per day, e.g., 1-20 MME per day. Or, for instance, wherein the current opioid dose not to be increased is less than 20 morphine milligram equivalents (MME) per day.

1.32 Any of Method 3, 1.1-1.13, 1.25, 1.26, or 1.31, wherein the current opioid dose not to be increased is 1-40 morphine milligram equivalents (MME) per day, e.g., 1-36 MME per day, e.g., 1-20 MME per day e.g., 10-20 MME per day.

1.33 Any of Method 4, 1.1-1.13, 1.25, or 1.26, wherein the opioid dose is not escalated above 50 morphine milligram equivalents (MME) per day, e.g., not escalated above 40 MME per day, e.g., not escalated above 36 MME per day, e.g., not escalated above 30 MME per day, e.g., not escalated above 20 MME per day.

1.34 Any of Method 5, 13, 17, 1.1-1.13, 1.25, or 1.26, wherein the method comprises reducing daily opioid dose by 2% to 10% over 4 to 8 weeks after starting administration of (1R,5S)-1-(3,4-dichlorophenyl)-3-azabicyclo[3.1.0]hexane, in free or pharmaceutically acceptable salt form. For instance, wherein the method comprises reducing daily opioid dose by 10% over 4 weeks after starting administration of (1R,5S)-1-(3,4-dichlorophenyl)-3-azabicyclo[3.1.0]hexane, in free or pharmaceutically acceptable salt form. For instance, wherein the method comprises reducing daily opioid dose by 10% over 8 weeks after starting administration of (1R,5S)-1-(3,4-dichlorophenyl)-3-azabicyclo[3.1.0] hexane, in free or pharmaceutically acceptable salt form. For Method 17, the daily opioid dose is reduced until discontinuation.

1.35 Any of Method 5, 13, 17, 1.1-1.13, 1.25, or 1.26, wherein the method comprises reducing daily opioid dose by 5% to 20% over 4 weeks after starting administration of (1R,5S)-1-(3,4-dichlorophenyl)-3-azabicyclo[3.1.0]hexane, in free or pharmaceutically acceptable salt form. For Method 17, the daily opioid dose is reduced until discontinuation.

1.36 Any of Method 5, 13, 17, 1.1-1.13, 1.25, or 1.26, wherein the method comprises reducing daily opioid dose by 10% to 20% in a week after starting administration of (1R,5S)-1-(3,4-dichlorophenyl)-3-azabicyclo[3.1.0]hexane, in free or pharmaceutically acceptable salt form. For Method 17, the daily opioid dose is reduced until discontinuation.

1.37 Any of Method 5, 13, 17, 1.1-1.13, 1.25, or 1.26, wherein the method comprises reducing daily opioid dose by 20 to 50% and then reducing daily opioid dose by 10% to 20% daily after starting administration of (1R,5S)-1-(3,4-dichlorophenyl)-3-azabicyclo[3.1.0] hexane, in free or pharmaceutically acceptable salt form. For Method 17, the daily opioid dose is reduced until discontinuation.

1.38 Any of Method 5, 13, 17, 1.1-1.13, 1.25, 1.26, or 1.34-1.37, wherein the method comprises reducing daily opioid dose by at least 10%, e.g., by at least 15%, 20%, 25%, 30%, 40%, or 50%, e.g., by 30% or more, e.g., by 30%, after starting administration of (1R,5S)-1-(3,4-dichlorophenyl)-3-azabicyclo[3.1.0]hexane, in free or pharmaceutically acceptable salt form. For instance, wherein the method comprises within or after, for instance, 4 weeks, 8 weeks, 90 days, 5 months, 6 months, 1 year, or 18 months, of receiving (1R,5S)-1-(3,4-dichlorophenyl)-3-azabicyclo[3.1.0]hexane, in free or pharmaceutically acceptable salt form, reducing daily opioid dose by at least 10%, e.g., by at least 15%, 20%, 25%, 30%, 40%, or 50%, e.g., by 30% or more, e.g., by 30%. For instance, wherein the method comprises reducing daily opioid dose by at least 10%, e.g., by 20% or more, e.g., by 30% or more, e.g., by 40% or more (e.g., by 40%), e.g., by 50% or more (e.g., by 50%), within or after at least 5 months (e.g., 6 months) of receiving (1R,5S)-1-(3,4-dichlorophenyl)-3-azabicyclo[3.1.0]hexane, in free or pharmaceutically acceptable salt form. For instance, wherein the method comprises reducing daily opioid dose by 30% or more, e.g., by 40% or more (e.g., by 40%), e.g., by 50% or more (e.g., by 50%), within or after 6 months of receiving (1R,5S)-1-(3,4-dichlorophenyl)-3-azabicyclo[3.1.0] hexane, in free or pharmaceutically acceptable salt form. For instance, wherein the method comprises reducing daily opioid dose as shown in FIG. 1. For Method 17, the daily opioid dose is reduced until discontinuation.

1.39 Any of Method 5, 13, 1.1-1.13, 1.25, 1.26, or 1.34-1.38, wherein the method comprises reducing daily opioid dose to 50 morphine milligram equivalents (MME) or less per day, e.g., 20-50 MME per day, e.g., 40 MME or less per day, e.g., 20-40 MME per day, e.g., 20-30 MME per day. For instance, wherein the method comprises reducing daily opioid dose to 20 morphine milligram equivalents (MME) or less per day, e.g., 1-20 MME per day. Or, for instance, wherein the method comprises reducing daily opioid dose to less than 20 morphine milligram equivalents (MME) per day.

1.40 Any of Method 5, 13, 1.1-1.13, 1.25, 1.26, or 1.34-1.39, wherein the method comprises reducing daily opioid dose to 1-40 morphine milligram equivalents (MME) per day, e.g., 1-36 MME per day, e.g., 1-20 MME per day e.g., 10-20 MME per day.

1.41 Any of Method 5, 13, 17, 1.1-1.13, 1.25, 1.26, or 1.34-1.40, wherein the method comprises reducing total daily morphine equivalent dose (MED) by at least 10%, e.g., by at least 15%, 20%, 25%, 30%, 40%, or 50%, e.g., by at least 30%, e.g., by 30%. For instance, wherein the method comprises over, for instance, 4 weeks, 8 weeks, 90 days, 6 months, 1 year, or 18 months, of receiving (1R,5S)-1-(3,4-dichlorophenyl)-3-azabicyclo[3.1.0]hexane, in free or pharmaceutically acceptable salt form, the total daily morphine equivalent dose (MED) is reduced by at least 10%, e.g., by at least 15%, 20%, 25%, 30%, 40%, or 50%, e.g., by at least 30%, e.g., by 30%. For instance, wherein the method comprises reducing total daily morphine equivalent dose (MED) by at least 10%, e.g., by least 30%, e.g., by 40%, within or after at least 5 months (e.g., 6 months) of receiving (1R,5S)-1-(3,4-dichlorophenyl)-3-azabicyclo[3.1.0]hexane, in free or pharmaceutically acceptable salt form. For instance, wherein the method comprises reducing total daily morphine equivalent dose (MED) by at least 30%, e.g., by 40%, within or after 6 months of receiving (1R,5S)-1-(3,4-dichlorophenyl)-3-azabicyclo[3.1.0]hexane, in free or pharmaceutically acceptable salt form. For Method 17, total daily morphine equivalent dose (MED) is reduced until discontinuation.

1.42 Any of Method 5, 13, 17, 1.1-1.13, 1.25, 1.26, or 1.34-1.41, wherein the patient's daily opioid dose escalated prior to administration of (1R,5S)-1-(3,4-dichlorophenyl)-3-azabicyclo[3.1.0]hexane, in free or pharmaceutically acceptable salt form.

1.43 Any of Method 5, 13, 17, 1.1-1.13, 1.25, 1.26, or 1.34-1.42, wherein the patient's daily opioid dose prior to reduction or discontinuation is 50 morphine milligram equivalents (MME) or more per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient's daily opioid dose prior to reduction is more than 50 to less than 90 MME per day. Or, for instance, wherein the patient's daily opioid dose prior to reduction or discontinuation is 50 morphine milligram equivalents (MME) or more per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.44 Any of Method 5, 13, 17, 1.1-1.13, 1.25, 1.26, or 1.34-1.43, wherein the patient has decreased pain severity, decreased pain interference, decreased anxiety, decreased depression, and improved quality of life with administration of (1R,5S)-1-(3,4-dichlorophenyl)-3-azabicyclo[3.1.0]hexane, in free or pharmaceutically acceptable salt form.

1.45 Any of Method 6, 1.1-1.13, 1.25, or 1.26, wherein the duration of opioid treatment is reduced to 2 years or less, e.g., 18 months or less, e.g., 1 year or less, e.g., 6 months or less.

1.46 Any of Method 6, 1.1-1.13, 1.25, 1.26, or 1.45, wherein the duration of opioid treatment is reduced to 3 months or less.

1.47 Any of Method 6, 1.1-1.13, 1.25, 1.26, 1.45, or 1.46, wherein the duration of opioid treatment is reduced to 6 weeks or less.

1.48 Any of Method 6, 1.1-1.13, 1.25, 1.26, or 1.45-1.47, wherein the duration of opioid treatment is reduced to 2 weeks or less.

1.49 Any of Method 7, 1.1-1.13, 1.25, or 1.26, wherein the patient is taking or is expected to take 50 morphine milligram equivalents (MME) or more of the opioid per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of the opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.50 Any of Method 8-11, 1.1-1.13, 1.25, or 1.26, wherein the patient is taking or is expected to take 50 morphine milligram equivalents (MME) or more of the opioid per day, e.g., more than 50 MME per day, e.g., 90 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of the opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.51 Any of Method 9, 10, 1.1-1.13, 1.25, 1.26, or 1.50, wherein the depression is new-onset depression.

1.52 Any of Method 9, 10, 1.1-1.13, 1.25, 1.26, 1.50, or 1.51, wherein the patient does not have a history of depression.

1.53 Any of Method 8-11, 1.1-1.13, 1.25, 1.26, or 1.50-1.52, wherein the patient is taking the opioid and (1R,5S)-1-(3,4-dichlorophenyl)-3-azabicyclo[3.1.0]hexane, in free or pharmaceutically acceptable salt form, is coordinately administered with the opioid.

1.54 Any of Method 13, 1.1-1.13, 1.25, 1.26, or 1.34-1.44, wherein the withdrawal symptoms are one or more of anxiety, negative affect, depression, dysphoria, weight gain, anhedonia, impulsivity, increase in appetite, increase in smoking, and increase in alcohol use.

1.55 Any of Method 13, 1.1-1.13, 1.25, 1.26, 1.34-1.44, or 1.54, wherein the daily opioid dose is being reduced by at least 10%, e.g., by at least 15%, 20%, 25%, 30%, 40%, or 50% or higher, e.g., by at least 30%, e.g., by 30%.

1.56 Any of Method 13, 1.1-1.13, 1.25, 1.26, 1.34-1.44, 1.54, or 1.55, wherein the daily opioid dose is being reduced by 2% to 10% every 4 to 8 weeks. For instance, wherein the daily opioid dose is being reduced by 10% every 4 weeks. For instance, wherein the daily opioid dose is being reduced by 10% every 8 weeks.

1.57 Any of Method 13, 1.1-1.13, 1.25, 1.26, 1.34-1.44, 1.54, or 1.55, wherein the daily opioid dose is being reduced by 5% to 20% every 4 weeks.

1.58 Any of Method 13, 1.1-1.13, 1.25, 1.26, 1.34-1.44, 1.54, or 1.55 wherein the daily opioid dose is being reduced by 10% to 20% every week.

1.59 Any of Method 13, 1.1-1.13, 1.25, 1.26, 1.34-1.44, 1.54, or 1.55, wherein the daily opioid dose is reduced by 20% to 50% and then reduced by 10% to 20% every day.

1.60 Any of Method 13, 1.1-1.13, 1.25, 1.26, 1.34-1.44, or 1.54-1.59, wherein the daily opioid dose prior to the opioid taper was 50 morphine milligram equivalents (MME) or more per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the daily opioid dose prior to the opioid taper was more than 50 to less than 90 MME per day. Or, for instance, wherein the daily opioid dose prior to the opioid taper was 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.61 Any of Method 13, 1.1-1.13, 1.25, 1.26, 1.34-1.44, or 1.54-1.60, wherein the method comprises reducing the daily opioid dose to 50 morphine milligram equivalents (MME) or less per day, e.g., 20-50 MME per day, e.g., 40 MME or less per day, e.g., 20-40 MME per day, e.g., 20-30 MME per day. For instance, wherein the method comprises reducing the daily opioid dose 20 morphine milligram equivalents (MME) or less per day, e.g., 1-20 MME per day. Or, for instance, wherein the method comprises reducing the daily opioid dose to less than 20 morphine milligram equivalents (MME) per day.

1.62 Any of Method 13, 1.1-1.13, 1.25, 1.26, 1.34-1.44, or 1.54-1.61, wherein the method comprises reducing the daily opioid dose to 1-40 morphine milligram equivalents per day, e.g., 1-36 MME per day, e.g., 1-20 MME per day, e.g., 10-20 MME per day.

1.63 Any of Method 14, 1.1-1.13, 1.25, or 1.26, wherein the patient is on opioid taper for opioid dose reduction or opioid discontinuation (e.g., wherein the opioid taper or opioid discontinuation is as described in any of Method 5, 17, or 1.34-1.44).

1.64 Any of Method 14, 1.1-1.13, 1.25, 1.26, or 1.63, wherein the daily opioid dose is being reduced by at least 10%, e.g., by at least 15%, 20%, 25%, 30%, 40%, or 50% or higher, e.g., by at least 30%, e.g., by 30%.

1.65 Any of Method 14, 1.1-1.13, 1.25, 1.26, 1.63, or 1.64, wherein the daily opioid dose is being reduced by 2% to 10% every 4 to 8 weeks. For instance, wherein the daily opioid dose is being reduced by 10% every 4 weeks. For instance, wherein the daily opioid dose is being reduced by 10% every 8 weeks.

1.66 Any of Method 14, 1.1-1.13, 1.25, 1.26, 1.63, or 1.64, wherein the daily opioid dose is being reduced by 5% to 20% every 4 weeks.

1.67 Any of Method 14, 1.1-1.13, 1.25, 1.26, 1.63, or 1.64, wherein the daily opioid dose is being reduced by 10% to 20% every week.

1.68 Any of Method 14, 1.1-1.13, 1.25, 1.26, 1.63, or 1.64, wherein the daily opioid dose is reduced by 20% to 50% and then reduced by 10% to 20% every day.

1.69 Any of Method 14, 1.1-1.13, 1.25, 1.26, or 1.63-1.68, wherein the daily opioid dose prior to the opioid taper was 50 morphine milligram equivalents (MME) or more per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the daily opioid dose prior to the opioid taper was more than 50 to less than 90 MME per day. Or, for instance, wherein the daily opioid dose prior to the opioid taper was 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.70 Any of Method 14, 1.1-1.13, 1.25, 1.26, or 1.63-1.69, wherein the method comprises reducing the daily opioid dose to 50 morphine milligram equivalents (MME) or less per day, e.g., 20-50 MME per day, e.g., 40 MME or less per day, e.g., 20-40 MME per day, e.g., 20-30 MME per day. For instance, wherein the method comprises reducing the daily opioid dose to 20 morphine milligram equivalents (MME) or less per day, e.g., 1-20 MME per day. Or, for instance, wherein the method comprises reducing the daily opioid dose to less than 20 morphine milligram equivalents (MME) per day.

1.71 Any of Method 14, 1.1-1.13, 1.25, 1.26, or 1.63-1.70, wherein the method comprises reducing the daily opioid dose to 1-40 morphine milligram equivalents per day, e.g., 1-36 MME per day, e.g., 1-20 MME per day, e.g., 10-20 MME per day.

1.72 Any of Method 15, 1.1-1.13, 1.25, or 1.26, wherein the (1R,5S)-1-(3,4-dichlorophenyl)-3-azabicyclo[3.1.0]hexane, in free or pharmaceutically acceptable salt form, and the opioid is administered for greater than 90 days, e.g., at least 12 weeks, e.g., at least 6 months, e.g., at least 1 year, e.g., at least 18 months, e.g., at least 2 years.

1.73 Any of Method 15, 1.1-1.13, 1.25, 1.26, or 1.72, wherein the dose of the opioid does not exceed 50 morphine milligram equivalents (MME) per day, e.g., the dose of the opioid is 20-50 MME per day, e.g., 40 MME or less per day, e.g., 20-40 MME per day, e.g., 20-30 MME per day. For instance, wherein the dose of the opioid does not exceed 20 morphine milligram equivalents (MME) per day, e.g., the dose of the opioid is 1-20 MME per day. Or, for instance, wherein the dose of the opioid is less than 20 morphine milligram equivalents (MME) per day. Or, for instance, wherein the dose of the opioid is 1-40 morphine milligram equivalents per day, e.g., 1-36 MME per day, e.g., 1-20 MME per day, e.g., 10-20 MME per day.

1.74 Any of Method 16, 1.1-1.13, 1.25, or 1.26, wherein the patient has taken or is expected to take the opioid for at least 2 weeks, e.g., at least 6 weeks, e.g., at least 90 days, e.g., greater than 90 days, e.g., at least 12 weeks, e.g., at least 6 months, e.g., at least 1 year, e.g., greater than 1 year, e.g., at least 18 months, e.g., at least 2 years.

1.75 Any of Method 16, 1.1-1.13, 1.25, 1.26, or 1.74, wherein the patient is taking or is expected to take 50 morphine milligram equivalents (MME) or more of the opioid per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of the opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.76 Any of Method 18, 1.1-1.13, 1.25, or 1.26, wherein the long-term risk of opioid use is one or more of opioid-induced hyperalgesia, depression, sexual dysfunction, hypogonadism, a fall, and a fracture.

1.77 Any of Method 18, 1.1-1.13, 1.25, 1.26, or 1.76, wherein the patient has taken or is expected to take the opioid for at least 2 weeks, e.g., at least 6 weeks, e.g., at least 90 days, e.g., greater than 90 days, e.g., at least 12 weeks, e.g., at least 6 months, e.g., at least 1 year, e.g., greater than 1 year, e.g., at least 18 months, e.g., at least 2 years.

1.78 Any of Method 18, 1.1-1.13, 1.25, 1.26, 1.76, or 1.77, wherein the patient is taking or is expected to take 50 morphine milligram equivalents (MME) or more of the opioid per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of the opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.79 Any of Method 19, 1.1-1.13, 1.25, or 1.26, wherein the daily opioid dose is not increased over at least 4 weeks, e.g., over at least 8 weeks, e.g., over at least 90 days, e.g., over at least 12 weeks, e.g., over at least 6 months, e.g., over at least 1 year, e.g., over at least 18 months, e.g., over at least 2 years.

1.80 Any of Method 19-22, 1.1-1.13, 1.25, 1.26, or 1.79, wherein the patient has taken or is expected to take the opioid for at least 2 weeks, e.g., at least 6 weeks, e.g., at least 90 days, e.g., greater than 90 days, e.g., at least 12 weeks, e.g., at least 6 months, e.g., at least 1 year, e.g., greater than 1 year, e.g., at least 18 months, e.g., at least 2 years.

1.81 Any of Method 19-22, 1.1-1.13, 1.25, 1.26, 1.79, or 1.80, wherein the patient is taking or is expected to take 50 morphine milligram equivalents (MME) or more of the opioid per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of the opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.82 Any of Method 23 or 1.1-1.11, wherein the patient has been treated with buprenorphine for opioid addiction and is seeking to discontinue buprenorphine. Any of Method 23 or 1.1-1.11, wherein the patient has been treated with methadone, buprenorphine/naloxone, and/or naltrexone for opioid addiction and is seeking to discontinue methadone, buprenorphine/naloxone, and/or naltrexone.

1.83 Any of Method 24-27, 1.25, 1.26, or 1.1-1.13, wherein the patient has taken or is expected to take an opioid for at least 2 weeks, e.g., at least 6 weeks, e.g., at least 90 days, e.g., greater than 90 days, e.g., at least 12 weeks, e.g., at least 6 months, e.g., at least 1 year, e.g., greater than 1 year, e.g., at least 18 months, e.g., at least 2 years.

1.84 Any of Method 24-27, 1.1-1.13, 1.25, 1.26, or 1.83, wherein the patient is taking or is expected to take 50 morphine milligram equivalents (MME) or more of an opioid per day, e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., 50 to 500 MME per day for at least 90 days (e.g., for greater than 90 days), e.g., more than 50 MME per day to 500 MME per day, e.g., more than 50 MME per day to 500 MME per day for at least 90 days (e.g., for greater than 90 days). For instance, wherein the patient is taking or is expected to take more than 50 to less than 90 MME of an opioid per day. Or, for instance, wherein the patient is taking or is expected to take 50 morphine milligram equivalents (MME) or more of the opioid per day (e.g., more than 50 MME per day, e.g., 60 MME or more per day, e.g., 90 MME or more per day, e.g., 100 MME or more per day, e.g., 120 MME or more per day, e.g., 200 MME or more per day, e.g., 50 to 90, 99, 100, 120, 200, 300, 400, or 500 MME per day, e.g., 50 to 500 MME per day, e.g., more than 50 MME per day to 500 MME per day) for at least 90 days (e.g., for greater than 90 days).

1.85 Any of Method 5, 13, 17, 1.1-1.13, 1.25, 1.26, or 1.34-1.44, wherein the method comprises reducing an original daily opioid dose by at least 10% (e.g., by 10%) within or after 4 weeks of starting administration of (1R,5S)-1-(3,4-dichlorophenyl)-3-azabicyclo[3.1.0]hexane, in free or pharmaceutically acceptable salt form, and optionally further reducing the original daily opioid dose by at least 20% (e.g., by 20%) within or after 8 weeks of starting administration of (1R,5S)-1-(3,4-dichlorophenyl)-3-azabicyclo[3.1.0]hexane, in free or pharmaceutically acceptable salt form, and optionally further reducing the original daily opioid dose by at least 30% (e.g., by 30%) within or after 12 weeks of starting administration of (1R,5S)-1-(3,4-dichlorophenyl)-3-azabicyclo[3.1.0]hexane, in free or pharmaceutically acceptable salt form, and optionally further reducing the original daily opioid dose by at least 40% (e.g., by 40%) within or after 16 weeks of starting administration of (1R,5S)-1-(3,4-dichlorophenyl)-3-azabicyclo[3.1.0]hexane, in free or pharmaceutically acceptable salt form, and optionally further reducing the original daily opioid dose by at least 50% (e.g., by 50%) within or after 20 weeks of starting administration of (1R,5S)-1-(3,4-dichlorophenyl)-3-azabicyclo[3.1.0]hexane, in free or pharmaceutically acceptable salt form. Or any of Method 5, 13, 17, 1.1-1.13, or 1.34-1.44, wherein within at least 5 months (e.g., 6 months) of starting administration of (1R,5S)-1-(3,4-dichlorophenyl)-3-azabicyclo[3.1.0]hexane, in free or pharmaceutically acceptable salt form, the daily opioid dose is reduced by at least 10%, e.g., by at least 30% (e.g., by 30%), e.g., by at least 40% (e.g., by 40%), e.g., by at least 50% (e.g., by 50%). For instance, wherein within or after 6 months of starting administration (1R,5S)-1-(3,4-dichlorophenyl)-3-azabicyclo[3.1.0]hexane, in free or pharmaceutically acceptable salt form, the daily opioid dose is reduced by at least 30% (e.g., by 30%), e.g., by at least 40% (e.g., by 40%). Or any of Method 5, 13, 17, 1.1-1.13, or 1.34-1.44, wherein the daily opioid dose is reduced by at least 10% (e.g., by 10%), e.g., by at least 20% (e.g., by 20%), e.g., by at least 30% (e.g., by 30%), e.g., by at least 40% (e.g., by 40%), e.g., by at least 50% (e.g., by 50%). Or any of Method 5, 13, 17, 1.1-1.13, or 1.34-1.44, wherein the daily opioid dose is reduced by at least 10% (e.g., by 10%), e.g., by at least 20% (e.g., by 20%), e.g., by at least 30% (e.g., by 30%), e.g., by at least 40% (e.g., by 40%), e.g., by at least 50% (e.g., by 50%), within 1 year (e.g., within 8 months, e.g., within 6 months, e.g., within 5 months, e.g., within 4 months, e.g., within 3 months, e.g., within 2 months, e.g., within 1 month) of starting administration of (1R,5S)-1-(3,4-dichlorophenyl)-3-azabicyclo[3.1.0]hexane, in free or pharmaceutically acceptable salt form. Or any of Method 5, 13, 17, 1.1-1.13, or 1.34-1.44, wherein the method comprises reducing daily opioid dose by at least 10% (e.g., by 10%) within or after 4 weeks of starting administration of (1R,5S)-1-(3,4-dichlorophenyl)-3-azabicyclo[3.1.0]hexane, in free or pharmaceutically acceptable salt form, and optionally then reducing current daily opioid dose by another 10% within or after 8 weeks of starting administration of (1R,5S)-1-(3,4-dichlorophenyl)-3-azabicyclo[3.1.0]hexane, in free or pharmaceutically acceptable salt form, and optionally then reducing current daily opioid dose by another 10% within or after 12 weeks of starting administration of (1R,5S)-1-(3,4-dichlorophenyl)-3-azabicyclo[3.1.0]hexane, in free or pharmaceutically acceptable salt form, and optionally then reducing current daily opioid dose by another 10% within or after 16 weeks of starting administration of (1R,5S)-1-(3,4-dichlorophenyl)-3-azabicyclo[3.1.0]hexane, in free or pharmaceutically acceptable salt form, and optionally then reducing current daily opioid dose by another 10% within or after 20 weeks of starting administration of (1R,5S)-1-(3,4-dichlorophenyl)-3-azabicyclo[3.1.0]hexane, in free or pharmaceutically acceptable salt form. For Method 17, the daily opioid dose is reduced until discontinuation.

1.86 Any of Method 1-27 or 1.1-1.85, wherein the patient has co-morbid depression (e.g., the patient has significant depressive symptoms, e.g., the patient has a Quick Inventory of Depressive Symptomatology (QIDS) score of equal to or greater than 5). For instance, wherein the patient has major depressive disorder.

1.87 Any of Method 1-27 or 1.1-1.86, wherein the patient has co-morbid alcohol dependence.

1.88 Any of Method 1-27 or 1.1-1.87, wherein the patient has co-morbid anxiety.

1.89 Any of Method 1-27 or 1.1-1.88, wherein the patient is human.

1.90 Any of Method 1-27 or 1.1-1.89, wherein the patient is female.

1.91 Any of Method 1-27 or 1.1-1.90, wherein the patient is overweight (e.g., BMI equal to or greater than 25).

1.92 Any of Method 1-27 or 1.1-1.91, wherein the patient has sleep apnea.

1.93 Any of Method 1-27 or 1.1-1.92, wherein the patient is 45 or older, e.g., 45-54.

1.94 Any of Method 1-27 or 1.1-1.93, wherein the patient is 55 or older, e.g., 55-64.

1.95 Any of Method 1-27 or 1.1-1.94, wherein (1R,5S)-1-(3,4-dichlorophenyl)-3-azabicyclo[3.1.0]hexane, in free or pharmaceutically acceptable salt form, is coordinately administered with a treatment for opioid use disorder (e.g., buprenorphine, naltrexone, methadone, and/or buprenorphine/naloxone).

1.96 Any of Method 1-27 or 1.1-1.95, wherein (1R,5S)-1-(3,4-dichlorophenyl)-3-azabicyclo[3.1.0]hexane, in free or pharmaceutically acceptable salt form, is coordinately administered with a partial opioid agonist (e.g., buprenorphine).

1.97 Any of Method 1-27 or 1.1-1.96, wherein the patient concurrently undergoes behavioral support, e.g., prescription opioid taper support (see, e.g., Sullivan, M. et al., J Pain., 2017, 18 (3), 308-318, which is hereby incorporated by reference in its entirety).

1.98 Any of Method 1-27 or 1.1-1.97, wherein the pain is neuropathic pain.

1.99 Any of Method 1-27 or 1.1-1.98, wherein the patient is not addicted to or dependent on the opioid.

1.100 Any of Method 1-27 or 1.1-1.99, wherein the patient does not have opioid use disorder.

1.101 Any of Method 1-27 or 1.1-1.100, wherein the patient does not have moderate or severe opioid use disorder. For instance, any of Method 1-27 or 1.1-1.100, wherein the patient does not have severe opioid use disorder.

1.102 Any of Method 1-27 or 1.1-1.101, wherein the patient is treated with (1R,5S)-1-(3,4-dichlorophenyl)-3-azabicyclo[3.1.0]hexane, in free or pharmaceutically acceptable salt form, before the patient has developed opioid use disorder.

1.103 Any of Method 1-27 or 1.1-1.98, wherein the patient does not have opioid use disorder, has mild opioid use disorder, or has moderate opioid use disorder. For instance, any of Method 1-27 or 1.1-1.98, wherein the patient has mild opioid use disorder or has moderate opioid use disorder. For instance, any of Method 1-27 or 1.1-1.98, wherein the patient does not have opioid use disorder or has mild opioid use disorder.

1.104 Any of Method 1-27 or 1.1-1.98, wherein the patient has mild opioid use disorder.

1.105 Any of Method 1-27 or 1.1-1.98, wherein the patient has moderate opioid use disorder.

1.106 Any of Method 1-27 or 1.1-1.105, wherein the method results in decreasing usage of rescue medication (e.g., a pain reliever that works quickly and may last for a short period of time) (e.g., ibuprofen, naproxen, and/or acetaminophen).

Also provided herein is use of (1R,5S)-1-(3,4-dichlorophenyl)-3-azabicyclo[3.1.0]hexane, in free or pharmaceutically acceptable salt form, in the manufacture of a medicament for use in any of Method 1-27 or 1.1-1.106.

Also provided herein is a pharmaceutical composition comprising (1R,5S)-1-(3,4-dichlorophenyl)-3-azabicyclo[3.1.0]hexane, in free or pharmaceutically acceptable salt form, in combination with a pharmaceutically acceptable diluent or carrier for use in any of Method 1-27 or 1.1-1.106.

Also provided herein is use of (1R,5S)-1-(3,4-dichlorophenyl)-3-azabicyclo[3.1.0]hexane, in free or pharmaceutically acceptable salt form, in any of Method 1-27 or 1.1-1.106.

Also provided herein is use of an opioid in the manufacture of a medicament for use in any of Method 1-27 or 1.1-1.106.

Also provided herein is a pharmaceutical composition comprising an opioid in combination with a pharmaceutically acceptable diluent or carrier for use in any of Method 1-27 or 1.1-1.106.

Also provided herein is use of an opioid in any of Method 1-27 or 1.1-1.106.

Also provided herein is use of (1R,5S)-1-(3,4-dichlorophenyl)-3-azabicyclo[3.1.0]hexane, in free or pharmaceutically acceptable salt form, and/or an opioid in the manufacture of a medicament for use in any of Method 1-27 or 1.1-1.106.

Also provided herein is a pharmaceutical composition comprising (1R,5S)-1-(3,4-dichlorophenyl)-3-azabicyclo[3.1.0]hexane, in free or pharmaceutically acceptable salt form, and/or an opioid in combination with a pharmaceutically acceptable diluent or carrier for use in any of Method 1-27 or 1.1-1.106.

Also provided herein is use of (1R,5S)-1-(3,4-dichlorophenyl)-3-azabicyclo[3.1.0]hexane, in free or pharmaceutically acceptable salt form, and/or an opioid in any of Method 1-27 or 1.1-1.106.

Dosages employed in practicing the present disclosure will vary depending, for example, on the mode of administration and the therapy desired. A daily dosage of (1R,5S)-1-(3,4-dichlorophenyl)-3-azabicyclo[3.1.0]hexane, in free or pharmaceutically acceptable salt form, for oral administration may be in the range of from 75 to 200 mg per day, for example, 100 mg to 200 mg per day, for example, 150 mg per day, conveniently administered once or in divided doses 2 to 6 times daily, optionally in sustained release form. Unit dosage forms for oral administration thus may comprise from, for example, 25 mg to 200 mg, for example, from 25 mg or 50 mg or 75 mg or 100 mg or 150 mg to 200 mg, for example, from 100 mg to 150 mg, of (1R,5S)-1-(3,4-dichlorophenyl)-3-azabicyclo[3.1.0]hexane, in free or pharmaceutically acceptable salt form, together with a pharmaceutically acceptable diluent or carrier therefor.

A method of administration of the dose of the present disclosure is not particularly limited. (1R,5S)-1-(3,4-dichlorophenyl)-3-azabicyclo[3.1.0]hexane, in free or pharmaceutically acceptable salt form, may be administered by any suitable route, including orally, parenterally, transdermally, inhalation, slow release, controlled release, although various other known delivery routes, devices and methods can likewise be employed. In some embodiments, provided is an oral sustained release pharmaceutical composition comprising (1R,5S)-1-(3,4-dichlorophenyl)-3-azabicyclo[3.1.0]hexane, in free or pharmaceutically acceptable salt form. In some embodiments, provided is an oral immediate release pharmaceutical composition comprising (1R,5S)-1-(3,4-dichlorophenyl)-3-azabicyclo[3.1.0]hexane, in free or pharmaceutically acceptable salt form.

Pharmaceutical compositions comprising (1R,5S)-1-(3,4-dichlorophenyl)-3-azabicyclo[3.1.0]hexane, in free or pharmaceutically acceptable salt form, may be prepared using conventional diluents or excipients and techniques known in the galenic art. Thus, oral dosage forms may include tablets, capsules, solutions, suspensions, and the like.

EXAMPLES

Example 1—Prescription Opioid Taper Trial: Adjunctive Treatment with Amitifadine and Prescription Opioid Taper Support to Reduce Opioid Dose, Risk for Opioid Use Disorder and Overdose in Adults with Chronic Non-Cancer Pain A multi-center, double-blind, placebo-controlled, parallel group design randomized controlled trial of amitifadine (AMI) at 150 mg/day or identical placebo in adults with chronic non-cancer pain (CNCP) on chronic high dose oral opioids (at doses of equal to or >50 MME/day (e.g., doses of 50-500 MME/day) for >90 days) added to open label prescription opioid taper support (POTS). The primary hypothesis is that AMI combined with POTS will have a greater effect than placebo plus POTS on reduced prescription opioid dose (primary), pain severity, pain interference, anxiety, depression, opioid misuse, and opioid use disorder (OUD) symptoms and improved quality of life. Reduced chronic opioid dose will significantly reduce risk of OUD and opioid overdose (OOD), significantly reducing the iatrogenic contribution to the opioid epidemic stemming from chronic high dose opioid therapy for CNCP.

Overview. A 6-month, randomized, double-blind, placebo controlled, parallel group, Phase IIb trial of the effects of amitifadine (AMI), 75 mg bid, when added to a manualized prescription opioid taper support (POTS) for opioid dose reduction in adults with CNCP on stable prescription opioid doses of 50-500 MME/day for >90 days. See FIG. 1.

Participants and Recruitment. Adults with CNCP, aged 18-70, who are taking opioid analgesic medications at a stable dose of 50-500 MME/day for >90 days, who are willing to consider tapering their opioid dose, will be recruited from primary care settings.

| Inclusion | Exclusion |
|---|---|
| Age 18-70 years | Cancer or terminal illness |
| Chronic non-cancer pain (in back, neck, limb or joint, with pain on more than half the days in the past 6 months) | Use of antidepressant pharmacotherapy in the past 30 days (SSRI, SNRI, or tricyclics) |
| Chronic opioid therapy (Prescribed 50-500 MME/day in past 30 d, without more than 20% change in past 90 days, with use on more than half of the previous 90 days) | Use of parental, transdermal, or transmucosal opioids in the past 30 d |
| | Implanted device for pain control |
| | Surgery in past 30 days or planned in next 6 months |
| Willingness to make an opioid dose reduction | Suicide attempt or psychiatric hospitalization in past year or current suicidal ideation with specific plan or intent |
| Able to provide informed consent | |
| Able to self-administer medications | |
| 80% adherence to documentation of opioid dose daily with AiCure remote observed therapy during screening | Psychotic symptoms |
| | Aberrant urine drug test (negative for prescribed opioid or positive for non-prescribed or illicit substance) |
| | Use of buprenorphine or naltrexone in the past 30 d, or enrolled in methadone treatment program for OUD |
| | Moderate or severe opioid use disorder, current (DSM-5, by PRISM) |
| | Non-opioid substance use disorder, current (alcohol, benzodiazepine, stimulant) |
| | Abnormal EKG |

Adults with moderate or severe OUD will be excluded and referred for OUD treatment; many participants on COT who would benefit from tapering meet criteria for mild OUD by DSM-5 criteria and do not require immediate pivoting of care to OUD treatment.

Interventions

Study medication: Double-blind AMI will be titrated by the study clinician to a peak dose of 75 mg BID as follows: 25 mg BID (50 mg/day) for week 1, 50 mg BID (100 mg/day) for week 2, then 75 mg BID (150 mg/day) for weeks 3 through week 24, then tapered to 50 mg bid in week 25 and 25 mg bid in week 26, then finally discontinued.

Prescription Opioid Taper Support (POTS) is a manualized, weekly behavioral prescription opioid taper support intervention that can be attended in person, by phone, or by webex. POTS will be administered by the study therapists and will support behavioral self-management of pain, reducing opioid dose, and adherence to study medication. POTS is manualized and feasible to implement with fidelity in a RCT.

Opioid taper. During the monthly in-person clinician visits held from weeks 4-20 to taper opioid dose, the study clinician will work with participants to reduce by approximately 10% the dose of oral opioid analgesia and will evaluate tolerability of study medication (AMI or PBO). At the baseline visit (week 0), following eligibility determination and consent, the participant will be introduced to the process of opioid tapering.

At visits at weeks 4, 8, 12, 16, 20, if function QOL pain intensity has improved or not changed, a 10% dose reduction of opioid dose (10% of opioid dose at study start) will be initiated as per Sullivan, M. et al., J Pain., 2017, 18 (3), 308-318. Participants can pause their opioid dose taper at any point. However, participants will not be allowed to increase their opioid dose during the study. If a participant chooses to do so, they will be retained in the study for data collection following discontinuation of taper. Participants can drop out of the study at any point; those who choose to do so will be considered to have failed the taper protocol, and their opioid taper data and other data assessed prior to discontinuation will be included in the analyses. From weeks 24 to 26, study medication will be tapered and study staff will coordinate return to the primary care physician and consult on adjunctive therapy that may be beneficial for pain control and maintenance of opioid dose achieved in the trial.

Primary outcome (Aim 1a): Opioid dose. The primary continuous outcome will be change in total opioid dose, in mean daily morphine milligram equivalents (MME) in the past 7 days, from baseline to the end of the 6-month intervention (week 24). The choice of the primary outcome measure is based on the goal of reduced risk for OUD and OOD, as higher dose chronic opioid treatment (COT) is associated with greater OUD and OOD risk. Further, reducing opioid exposure will reduce other long-term risks of opioids such as opioid-induced depression, opioid-induced hyperalgesia, hypogonadism, falls, and fractures.

Endpoints:
  1°: Greater reduction in chronic opioid therapy dose compared to placebo
  2°: (1) Fewer opioid-related problems (opioid difficulties, opioid misuse, DSM-5 criteria for OUD/OOD events), (2) greater improvement in pain, pain interference, and pain-related function, (3) greater improvement in psychological functioning (quality of life, depression, anxiety, and sleep), (4) no greater incidence of AEs or study DC Example 2—Opioid Self-Administration In rats trained to self-administer an opioid, treatment with amitifadine significantly reduces self-administration.

It has been reported that amitifadine does not significantly affect food motivated responding at doses of 5 and 10 mg/kg (Levin, E. et al., "Amitifadine, a Triple Monoamine Reuptake Inhibitor, Reduces Nicotine Self-administration in Female Rats," European Journal of Pharmacology, 2015, 764, 30-37).

Example 3—Hot Plate Test of Analgesia

The hot plate test assesses antinociception in rats and mice (see, e.g., Basile, A. et al., "Characterization of the Antinociceptive Actions of Bicifadine in Models of Acute, Persistent, and Chronic Pain," The Journal of Pharmacology and Experimental Therapeutics, 2007, 321 (3), 1208-1225).

Amitifadine and an opioid are tested alone and in combination in the hot plate test in rats. Amitifadine and the opioid are antinociceptive when given alone and in combination. In combination, amitifadine does not attenuate the opioid's antinociception, instead extending the opioid's antinociception.

What is claimed is:

1. A method of reducing daily opioid dose in a patient being treated with an opioid, wherein the method comprises coordinately administering to the patient (1R,5S)-1-(3,4-dichlorophenyl)-3-azabicyclo[3.1.0]hexane, in free or pharmaceutically acceptable salt form, and the opioid.

2. A method of opioid discontinuation in a patient being treated with an opioid, wherein the method comprises coordinately administering to the patient (1R,5S)-1-(3,4-dichlorophenyl)-3-azabicyclo[3.1.0]hexane, in free or pharmaceutically acceptable salt form, and the opioid until the opioid is discontinued.

3. The method of claim 1 or 2, wherein the method comprises reducing daily opioid dose by 2% to 10% over 4 to 8 weeks after starting administration of (1R,5S)-1-(3,4-dichlorophenyl)-3-azabicyclo[3.1.0]hexane, in free or pharmaceutically acceptable salt form.

4. The method of claim 1 or 2, wherein the method comprises reducing daily opioid dose by at least 10% over 4 weeks after starting administration of (1R,5S)-1-(3,4-dichlorophenyl)-3-azabicyclo[3.1.0]hexane, in free or pharmaceutically acceptable salt form.

5. The method of claim 1 or claim 2, wherein the patient's daily opioid dose was escalated prior to administration of (1R,5S)-1-(3,4-dichlorophenyl)-3-azabicyclo[3.1.0] hexane, in free or pharmaceutically acceptable salt form.

6. The method of claim 1 or claim 2, wherein the patient's daily opioid dose prior to reduction or discontinuation is at least 50 morphine milligram equivalents (MME) per day.

7. The method of claim 1 or claim 2, wherein the daily opioid dose is reduced by at least 10%.

8. The method of claim 1 or claim 2, wherein the daily opioid dose is reduced by at least 30% within 6 months of starting administration of (1R,5S)-1-(3,4-dichlorophenyl)-3-azabicyclo[3.1.0]hexane, in free or pharmaceutically acceptable salt form.

9. The method of claim 1 or claim 2, wherein the patient has decreased pain severity, decreased pain interference, decreased anxiety, decreased depression, and improved quality of life with administration of (1R,5S)-1-(3,4-dichlorophenyl)-3-azabicyclo[3.1.0]hexane, in free or pharmaceutically acceptable salt form.

10. The method of claim 6, wherein the daily opioid dose is reduced by at least 50 MME per day for at least 90 days.

11. The method of claim 6, wherein the daily opioid dose is reduced by at least 50 to 500 MME per day for greater than 90 days.

12. The method of claim 7, wherein the daily opioid dose is reduced by at least by at least 20%.

13. The method of claim 7, wherein the daily opioid dose is reduced by at least 30%.

14. The method of claim 7, wherein the daily opioid dose is reduced by at least 40%.

15. The method of claim 7, wherein the daily opioid dose is reduced by at least 50%.

16. The method of claim 8, wherein the daily opioid dose is reduced by at least 30% within 6 months of starting administration of (1R,5S)-1-(3,4-dichlorophenyl)-3-azabicyclo[3.1.0]hexane, in free or pharmaceutically acceptable salt form.

17. The method of claim 8, wherein the daily opioid dose is reduced by at least 30% within 5 months of starting administration of (1R,5S)-1-(3,4-dichlorophenyl)-3-azabicyclo[3.1.0]hexane, in free or pharmaceutically acceptable salt form.

18. The method of claim 8, wherein the daily opioid dose is reduced by at least 30% within 4 months of starting administration of (1R,5S)-1-(3,4-dichlorophenyl)-3-azabicyclo[3.1.0]hexane, in free or pharmaceutically acceptable salt form.

19. The method of claim 8, wherein the daily opioid dose is reduced by at least 30% within 3 months of starting administration of (1R,5S)-1-(3,4-dichlorophenyl)-3-azabicyclo[3.1.0]hexane, in free or pharmaceutically acceptable salt form.

20. The method of claim 1 or claim 2, wherein the patient is being treated with the opioid to reduce chronic back pain.

21. The method of claim 20, wherein the patient is age 45 or older.

22. The method of claim 20, wherein the (1R,5S)-1-(3,4-dichlorophenyl)-3-azabicyclo[3.1.0]hexane, in free or pharmaceutically acceptable salt form, is administered at a dosage of from about 75 to 200 mg per day.

23. The method of claim 22, wherein the (1R,5S)-1-(3,4-dichlorophenyl)-3-azabicyclo[3.1.0]hexane, in free or pharmaceutically acceptable salt form, is administered at a dosage of from about 100 to 200 mg per day.

24. The method of claim 23, wherein the (1R,5S)-1-(3,4-dichlorophenyl)-3-azabicyclo[3.1.0]hexane, in free or pharmaceutically acceptable salt form, is administered at a dosage of about 150 mg per day.

25. The method of claim 20, wherein the opioid is hydrocodone, oxycodone, oxymorphone, morphine, codeine, fentanyl, levorphanol, tramadol, dihydrocodeine, meperidine, hydromorphone, tapentadol, remifentanil, buprenorphine, alfentanil, carfentanil or sufentanil.

26. The method of claim 25, wherein the opioid is oxycodone.

27. The method of claim 25, wherein the opioid is hydrocodone.

* * * * *